US010220056B2

(12) United States Patent
Ott et al.

(10) Patent No.: US 10,220,056 B2
(45) Date of Patent: *Mar. 5, 2019

(54) DECELLULARIZATION AND RECELLULARIZATION OF SOLID ORGANS

(71) Applicant: Miromatrix Medical Inc., Eden Prairie, MN (US)

(72) Inventors: Harald Ott, Boston, MA (US); Doris Taylor, St. Paul, MN (US)

(73) Assignee: Miromatrix Medical, Inc., Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/913,974

(22) Filed: Jun. 10, 2013

(65) Prior Publication Data

US 2013/0344599 A1    Dec. 26, 2013

Related U.S. Application Data

(63) Continuation of application No. 13/725,030, filed on Dec. 21, 2012, which is a continuation of application No. 12/064,613, filed as application No. PCT/US2006/033415 on Aug. 28, 2006, now Pat. No. 8,470,520.

(60) Provisional application No. 60/815,242, filed on Jun. 19, 2006, provisional application No. 60/711,501, filed on Aug. 26, 2005.

(51) Int. Cl.
| C12N 5/00 | (2006.01) |
| A61K 35/12 | (2015.01) |
| A61K 9/00 | (2006.01) |
| C12M 3/00 | (2006.01) |
| C12M 1/12 | (2006.01) |
| C12M 1/26 | (2006.01) |
| C12N 5/077 | (2010.01) |
| A61K 35/34 | (2015.01) |

(52) U.S. Cl.
CPC ............ *A61K 35/12* (2013.01); *A61K 9/0024* (2013.01); *C12M 21/08* (2013.01); *C12M 25/14* (2013.01); *C12M 33/04* (2013.01); *C12N 5/0657* (2013.01); *A61K 35/34* (2013.01); *C12N 2506/00* (2013.01); *C12N 2533/90* (2013.01)

(58) Field of Classification Search
CPC .............................. A61K 35/12; A61K 9/0024
See application file for complete search history.

(56) References Cited

U.S. PATENT DOCUMENTS

| 3,545,221 A | 12/1970 | Koski et al. |
| 3,639,084 A | 2/1972 | Goldhaber |
| 4,083,066 A | 4/1978 | Schmitz et al. |
| 4,801,299 A | 1/1989 | Brendel et al. |
| 5,336,616 A | 8/1994 | Livesey et al. |
| 6,376,244 B1 | 4/2002 | Atala |
| 6,379,963 B2 | 4/2002 | Haverich et al. |
| 6,416,995 B1 | 7/2002 | Wolfinbarger |
| 6,432,712 B1 | 8/2002 | Wolfinbarger, Jr. |
| 6,479,064 B1 | 11/2002 | Atala |
| 6,689,161 B2 | 2/2004 | Chen et al. |
| 6,749,064 B1 | 6/2004 | Alrey |
| 6,753,181 B2 | 6/2004 | Atala et al. |
| 6,960,427 B2 | 11/2005 | Haverich et al. |
| 6,962,814 B2 | 11/2005 | Mitchell et al. |
| 7,311,904 B2 | 12/2007 | Hariri |
| 7,354,749 B2 | 4/2008 | Fisher et al. |
| 8,470,520 B2 | 6/2013 | Ott et al. |
| 9,334,479 B2 | 5/2016 | Herrera Sanchez et al. |
| 2001/0049138 A1 | 12/2001 | Dennis et al. |
| 2002/0081728 A1 | 6/2002 | Haverich et al. |
| 2003/0087428 A1 | 5/2003 | Wolfinbarger, Jr. et al. |
| 2003/0096407 A1 | 5/2003 | Atala et al. |
| 2003/0124099 A1 | 7/2003 | Atala et al. |
| 2003/0215945 A1 | 11/2003 | Atala |
| 2003/0228692 A1 | 12/2003 | Goldstein et al. |
| 2004/0176855 A1 | 9/2004 | Badylak |
| 2004/0187877 A1 | 9/2004 | Badylak et al. |
| 2005/0084512 A1 | 4/2005 | Denizeau et al. |
| 2005/0249816 A1 | 11/2005 | Atala et al. |
| 2007/0020610 A1 | 1/2007 | Sherley et al. |
| 2007/0059293 A1 | 3/2007 | Atala |
| 2008/0058956 A1 | 3/2008 | Badylak |
| 2009/0169525 A1 | 7/2009 | Anversa et al. |
| 2009/0202977 A1 | 8/2009 | Ott et al. |
| 2011/0059152 A1 | 3/2011 | Atala |
| 2012/0183944 A1 | 7/2012 | Taylor et al. |
| 2013/0109088 A1 | 5/2013 | Ott et al. |
| 2013/0156744 A1 | 6/2013 | Taylor et al. |

FOREIGN PATENT DOCUMENTS

| AU | 2006282783 B2 | 9/2013 |
| AU | 2013224686 B2 | 6/2015 |
| CN | 1615162 A | 5/2005 |
| CN | 101066477 A | 11/2007 |
| CN | 101272815 A | 9/2008 |
| CN | 101272815 B | 9/2012 |
| CN | ZL200680030925.4 | 9/2012 |
| CN | 102861359 A | 1/2013 |
| EP | 1246903 A1 | 1/2008 |
| EP | 2431063 A2 | 3/2012 |
| EP | 1928519 B1 | 4/2012 |
| EP | 2431063 B1 | 6/2015 |
| EP | 2965769 A1 | 1/2016 |
| EP | 2611472 B1 | 2/2016 |

(Continued)

OTHER PUBLICATIONS

"U.S. Appl. No. 13/262,286, Non Final Office Action dated Oct. 9, 2014", 7 pgs.

(Continued)

*Primary Examiner* — Marcia S Noble
(74) *Attorney, Agent, or Firm* — Wilson Sonsini Goodrich & Rosati

(57) ABSTRACT

The invention provides for methods and materials to decellularize a solid organ and to recellularize such a decellularized organ to thereby generate a solid organ.

26 Claims, 2 Drawing Sheets

(56) References Cited

FOREIGN PATENT DOCUMENTS

| | | |
|---|---|---|
| ES | 2384721 T3 | 7/2012 |
| HK | 1170662 A | 3/2013 |
| JP | 5516016 A | 2/1980 |
| JP | 55-016016 A | 4/1980 |
| JP | 06-261933 A | 9/1994 |
| JP | H1176400 A | 3/1999 |
| JP | 2000004870 A | 1/2000 |
| JP | 2004-167236 A | 6/2004 |
| JP | 2005509495 A | 4/2005 |
| JP | 2007222391 A | 9/2007 |
| JP | 2008541717 A | 11/2008 |
| JP | 2009505752 A | 2/2009 |
| JP | 2013-536738 A | 6/2013 |
| JP | 2015094591 A | 5/2015 |
| JP | 2015164549 A | 9/2015 |
| JP | 2016039903 A | 3/2016 |
| JP | 2017038948 A | 2/2017 |
| JP | 6089062 B2 | 3/2017 |
| JP | 2017195900 A | 11/2017 |
| MX | 343363 B | 11/2016 |
| RU | 2463081 C2 | 10/2012 |
| RU | 2611361 C2 | 2/2017 |
| WO | WO-1996008213 A1 | 3/1996 |
| WO | WO-2001048153 A1 | 7/2001 |
| WO | WO-2001049210 A1 | 7/2001 |
| WO | WO-2002024244 A2 | 3/2002 |
| WO | WO-2002040630 A2 | 5/2002 |
| WO | WO-0249681 A1 | 6/2002 |
| WO | WO-2002049681 A1 | 6/2002 |
| WO | WO-02063962 A1 | 8/2002 |
| WO | WO-2002063962 A1 | 8/2002 |
| WO | WO-03039610 A1 | 5/2003 |
| WO | WO-03043674 A1 | 5/2003 |
| WO | WO-2003039610 A1 | 5/2003 |
| WO | WO-2003043674 A1 | 5/2003 |
| WO | WO-20030087428 A1 | 5/2003 |
| WO | WO-2004/054571 A1 | 7/2004 |
| WO | WO-2004080501 A1 | 9/2004 |
| WO | WO-2004100832 A1 | 11/2004 |
| WO | WO-2005118014 A2 | 12/2005 |
| WO | WO-2006033415 A1 | 3/2006 |
| WO | WO-2006122533 A2 | 11/2006 |
| WO | WO-2007025233 A1 | 3/2007 |
| WO | WO-2010120539 A1 | 10/2010 |
| WO | WO-2010120539 A2 | 10/2010 |
| WO | WO-2010-120539 A3 | 2/2011 |
| WO | WO-2010120539 A3 | 2/2011 |
| WO | WO-2011031484 A2 | 3/2011 |
| WO | WO-2012031162 A1 | 3/2012 |

OTHER PUBLICATIONS

"U.S. Appl. No. 13/725,030, Non Final Office Action dated Dec. 5, 2014", 19 pgs.
"U.S. Appl. No. 13/820,079, Non Final Office Action dated Oct. 23, 2014", 14 pgs.
"Australian Application Serial No. 2013224686, First Examiner Report dated Dec. 18, 2014", 2 pgs.
"European Serial No. 11181797.9, Office Action dated Jul. 16, 2012", 2 pgs.
"European Application Serial No. 11181797.9, Response filed Aug. 13, 2014 to Office Action dated Feb. 3, 2014", 13 pgs.
"Japanese Application Serial No. 2012-248398, Amendment and Argument filed Aug. 18, 2014", (w/ English Translation), 50 pgs.
Alberts, B., etal,. *In: Molecular Biology of the Cell*, (3rd Edition). Garland Publishing, New York and London, (1994), 971-977.
Liu, Xiaoqing, et al., "Elastic fiber homeostasis requires lysyl oxidase-like 1 protein", *Nature Genetics*, 36(2), (2004), 178-182.
"U.S. Appl. No. 13/262,286, Final Office Action dated Jun. 11, 2015", 6 pgs.
"U.S. Appl. No. 13/262,286, Response filed Mar. 9, 2015 to Non Final Office Action dated Oct. 9, 2014", 7 pgs.

"U.S. Appl. No. 13/725,030, Examiner Interview Summary dated Mar. 6, 2015", 3 pgs.
"U.S. Appl. No. 13/725,030, Final Office Action dated May 19, 2015", 23 pgs.
"U.S. Appl. No. 13/725,030, Response filed Mar. 4, 2015 to Non Final Office Action dated Dec. 5, 2014", 14 pgs.
"U.S. Appl. No. 13/820,079, Final Office Action dated Apr. 23, 2015", 15 pgs.
"U.S. Appl. No. 13/820,079, Response filed Jan. 22, 2015 to Non Final Office Action dated Oct. 23, 2014", 10 pgs.
"U.S. Appl. No. 13/820,079, Response filed Jul. 23, 2015 to Final Office Action dated Apr. 23, 2015", 10 pgs.
"Japanese Application Serial No. 2012-248398, Examiners Decision of Final Refusal dated Jan. 7, 2015", (w/ English Translation), 6 pgs.
"Japanese Application Serial No. 2015-94591, Amendment filed Jun. 5, 2015", (w/ English Translation), 5 pgs.
Bauer, A., et al., "hDAF porcine cardiac xenograft maintains cardiac output after orthotopic gtransplantation into a baboon—a perioperative study", (Abstract), *Xenotransplantation*, 12(6), 444-449, (2005), 1 pg.
Bonandrini, Barbara, et al., "Recellularization of Well-Preserved Acellular Kidney Scaffold Using Embryonic Stem Cells", *Tissue Engineering: Part A*, vol. 20, Nos. 9 and 10, (2014), 1486-1498.
Gilpin, Sarah E., et al., "Enhanced Lung Epithelial Specification of Human Induced Pluripotent Stem Cells on Decellularized Lung Matrix", *Ann Thorac Surg.*, 98, (2014), 721-729.
Robertson, Matthew J., et al., "Optimizing Recellularization of Whole Decellularized Heart Extracellular Matrix", *PLoS ONE*, 9(2): e90406, (Feb. 2014), 1-10.
Song, Jeremy J., et al., "Regeneration and experimental orthotopic transplantation of a bioengineered kidney", *Nature Medicine Advance Online Publication*, accepted Feb. 11, 2013; published online Apr. 14, 2013, (2013), 1-8.
Suresh, Vijayan, et al., "A retrospective study of the prognostic impact of cytokine secretion in mixed lymphocyte culture on long-term graft function following allogeneic renal transplantation", *Transpl Int.*,18(9), (2005), 1067-1071.
Wang, Yunfang, et al., "Lineage Restriction of Human Hepatic Stem Cells to Mature Fates Is Made Efficient by Tissue-Specific Biomatrix Scaffolds", *Hepatology*,53, (2011), 293-305.
Yasui, Haruyo, et al., "Excitation propagation in three-dimensional engineered hearts using decellularized matrix", *Biomaterials*, 35, (2014), 7839-7850.
"U.S. Appl. No. 13/262,286, Final Office Action dated Aug. 14, 2013", 9 pgs.
"U.S. Appl. No. 13/262,286, Preliminary Amendment filed Sep. 30, 2011", 3 pgs.
"U.S. Appl. No. 13/262,286, Response filed Feb. 14, 2014 to Final Office Action dated Aug. 14, 2013", 7 pgs.
"U.S. Appl. No. 13/725,030, Advisory Action dated Jun. 5, 2014", 3 pgs.
"U.S. Appl. No. 13/725,030, Final Office Action dated Mar. 17, 2014", 14 pgs.
"U.S. Appl. No. 13/725,030, Non Final Office Action dated Jul. 5, 2013", 12 pgs.
"U.S. Appl. No. 13/725,030, Response filed Jan. 2, 2014 to Non Final Office Action dated Jul. 5, 2013", 10 pgs.
"U.S. Appl. No. 13/725,030, Response filed May 19, 2014 to Final Office Action dated Mar. 17, 2014", 11 pgs.
"U.S. Appl. No. 13/820,079, Preliminary Amendment filed Feb. 28, 2013", 8 pgs.
"U.S. Appl. No. 13/820,079, Response filed Dec. 26, 2013 to Restriction Requirement dated Oct. 25, 2013", 9 pgs.
"U.S. Appl. No. 13/820,079, Restriction Requirement dated Oct. 25, 2013", 9 pgs.
"Australian Application Serial No. 2013224686, Voluntary Amendment filed Jun. 13, 2014", 15 pgs.
"Canadian Application Serial No. 2,618,731, Office Action dated Jun. 13, 2014", 2 pgs.
"Canadian Application Serial No. 2,618,731, Response filed Sep. 27, 2013 to Office Action dated Mar. 27, 2013", 20 pgs.

(56) References Cited

OTHER PUBLICATIONS

"Chinese Application Serial No. 201210287455.7, Office Action dated Nov. 14, 2013", (w/ English Translation), 11 pgs.
"Chinese Application Serial No. 201210287455.7, Response filed Mar. 31, 2014 to Office Action dated Nov. 14, 2013", (w/ English Translation of Amended Claims), 9 pgs.
"European Application Serial No. 06790024.1, Office Action dated Sep. 18, 2009", 1 pg.
"European Application Serial No. 06790024.1, Result of Consultation dated Nov. 30, 2009", 3 pgs.
"European Application Serial No. 11181797.9, Office Action dated Feb. 3, 2014", 4 pgs.
"European Application Serial No. 11181797.9, Response filed Jun. 26, 2013 to Office Action dated Feb. 21, 2013", 5 pgs.
"European Application Serial No. 11181797.9, Result of Consultation dated Jun. 26, 2014", 3 pgs.
"Indian Application Serial No. 1741/DELNP/2008, First Examiner Report dated Jun. 24, 2013", 3 pgs.
"Indian Application Serial No. 1741/DELNP/2008, Response filed May 28, 2014 to Office Action dated Jun. 24, 2013", 13 pgs.
"Israeli Application Serial No. 189418, Notification Prior to Refusal dated Jan. 13, 2014", 1 pg.
"Israeli Application Serial No. 189418, Response filed Feb. 9, 2014 to Office Action dated Apr. 7, 2013", (English Translation), 36 pgs.
"Japanese Application Serial No. 2012-248398, Amendment filed Jun. 25, 2013", (w/ English Translation of Amendment), 10 pgs.
"Japanese Application Serial No. 2012-248398, Notice of Reasons for Rejection dated Mar. 5, 2014", (w/ English Translation), 8 pgs.
"Korean Application Serial No. 10-2008-7007151, Office Action dated Jun. 27, 2013", (w/ English Translation), 4 pgs.
"Korean Application Serial No. 10-2008-7007151, Response filed Oct. 28, 2013 to Office Action dated Jun. 27, 2013", (w/ English Translation of Claims), 25 pgs.
"Korean Application Serial No. 10-2013-7028378, Notice of Preliminary Rejection dated Jan. 24, 2014", (w/ English Translation), 8 pgs.
"Korean Application Serial No. 10-2013-7028378, Response filed Mar. 24, 2014 to Notice of Preliminary Rejection dated Jan. 24, 2014", (w/ English Translation of the Claims), 28 pgs.
"Korean Application Serial No. 10-2014-7007674, Notice of Preliminary Rejection dated Jun. 24, 2014", (w/ English Translation), 4 pgs.
"Mexican Application Serial No. MX/a/2008/002589, Office Action dated Nov. 12, 2013", (w/ English Translation), 3 pgs.
"Mexican Application Serial No. MX/a/2008/002589 Response filed Jan. 22, 2014 to Office Action dated Nov. 12, 2013", (w/ English Translation of Amendments), 12 pgs.
"Russian Application Serial No. 2008111503, Response filed Jan. 16, 2012 to Office Action dated Oct. 27, 2011", (w/ English Translation of Amended Claims), 10 pgs.
Badylak, S. F., et al., "Whole-organ tissue engineering: decellularization and recellularization of three-dimensional matrix scaffolds", *Annu Rev Biomed Eng.*, 13, (2011), 27-53.
Baptista, P. M, et al., "Human liver bioengineering using a whole liver decellularized bioscaffold", *Methods Mol Biol.*, 1001, (Abstract Only), (2013), 1 pg.
Barakat, O., et al., "Use of Decellularized Porcine Liver for Engineering Humanized Liver Organ", *Journal of Surgical Research*, 173(1), (2012), e11-e25.
Bonvillain, R. W, et al,, "A nonhuman primate model of lung regeneration: detergent-mediated decellularization and initial in vitro recellularization with mesenchymal stem cells.", *Tissue Eng Part A.*, 18(23-24), (Abstract Only), (Dec. 2012), 1 pg.
Daly, A. B, et al., "Initial binding and recullarization of decellularized mouse lung scaffolds with bone marrow-derived mesenchymal stromal cells", *Tissue Eng Part A.*, 18(1-2), (Abstract Only), (Jan. 2012), 1 pg.
Faulk, D. M, et al., "Role of the Extracellular Matrix in Whole Organ Engineering", *J Cell Physiol.*, (Abstract Only), (Dec. 18, 2013), 1 pg.

Goh, S. K., et al., "Perfusion-decellularized pancreas as a natural 3D scaffold for pancreatic tissue and whole organ engineering.", *Biomaterials*, 34(28), (2013), 6760-6772.
Ott, H. C, et al., "Regeneration and orthotopic transplantation of a bioartificial lung", Nat Med., 16(8), (Abstract Only), (Aug. 2008), 1 pg.
Petersen, T. H, et al., "Tissue-engineered lungs for in vivo implantation", *Science*, 329(5991), (Abstract Only), (Jul. 30, 2010), 1 pg.
Seaberg, R. M., et al., "Stem and progenitor cells: the premature desertion of rigorous definitions", *TRENDS in Neurosciences*, 26(3), (Mar. 2003),125-131.
Song, J. J., et al., "Enhanced In Vivo Function of Bioartificial Lungs in Rats", *Ann. Thorac. Surg.*, 92(3), (2011), 998-1006.
Song, J. J, et al., "Regeneration and experimental orthotopic transplantation of a bioengineered kidney", *Nat Med.*, 19(5), (May 2013), 646-651.
Soto-Gutierrez, A., et al., "A Whole-Organ Regenerative Medicine Approach for Liver Replacement", *Tissue Endineering Part C: Methods*, 17(6), (2011), 677-686.
Uygun, B. E, et al., "Decellularization and recellularization of whole livers", *J Vis Exp.*, (48), (Abstract Only), (Feb. 2011), 1 pg.
Yagi, H., et al., "Human-Scale Whole-Organ Bioengineering for Liver Transplantation: A Regenerative Medicine Approach", *Cell Transplant.*, 22(2), (2013), 231-242.
"U.S. Appl. No. 12/064,613, Response filed Apr. 5, 2013 to Final Office Action dated Feb. 7, 2013", 11 pgs.
"U.S. Appl. No. 12/064,613, Examiner Interview Summary dated Mar. 7, 2013", 3 pgs.
"U.S. Appl. No. 12/064,613, Examiner Interview Summary dated Apr. 5, 2013", 4 pgs.
"U.S. Appl. No. 12/064,613, Examiner Interview Summary dated Jun. 20, 2012", 3 pgs.
"U.S. Appl. No. 12/064,613, Examiner Interview Summary dated Jul. 13, 2012", 3 pgs.
"U.S. Appl. No. 12/064,613, Examiner Interview Summary dated Jul. 18, 2012", 3 pgs.
"U.S. Appl. No. 12/064,613, Final Office Action dated Feb. 7, 2013", 16 pgs.
"U.S. Appl. No. 12/064,613, Final Office Action dated Apr. 6, 2012", 10 pgs.
"U.S. Appl. No. 12/064,613, Non Final Office Action dated Aug. 30, 2012", 19 pgs.
"U.S. Appl. No. 12/064,613, Non Final Office Action dated Sep. 29, 2011", 8 pgs.
"U.S. Appl. No. 12/064,613, Notice of Allowance dated May 1, 2013", 11 pgs.
"U.S. Appl. No. 12/064,613, Preliminary Amendment filed Feb. 22, 2008", 8 pgs.
"U.S. Appl. No. 12/064,613, Response filed Jan. 25, 2012 to Non Final Office Action dated Sep. 29, 2011", 10 pgs.
"U.S. Appl. No. 12/064,613, Response filed Jul. 16, 2012 to Final Office Action dated Apr. 16, 2012", 12 pgs.
"U.S. Appl. No. 12/064,613, Response filed Jul. 21, 2011 to Restriction Requirement dated Jun. 29, 2011", 13 pgs.
"U.S. Appl. No. 12/064,613, Response filed Dec. 4, 2012 to Non Final Office Action dated Aug. 30, 2012", 11 pgs.
"U.S. Appl. No. 12/064,613, Restriction Requirement dated Jun. 29, 2011", 8 pgs.
"U.S. Appl. No. 12/547,021, Final Office Action dated May 14, 2012", 11 pgs.
"U.S. Appl. No. 12/547,021, Non Final Office Action dated Dec. 14, 2011", 11 pgs.
"U.S. Appl. No. 12/547,021, Response filed Mar. 14, 2012 to Non Final Office Action dated Dec. 14, 2011", 9 pgs.
"U.S. Appl. No. 13/262,286, Non Final Office Action dated Dec. 14, 2012", 10 pgs.
"U.S. Appl. No. 13/262,286, Response filed Nov. 30, 2012 to Restriction Requirement dated Oct. 30, 2012", 8 pgs.
"U.S. Appl. No. 13/262,286, Restriction Requirement dated Oct. 30, 2012", 8 pgs.
"U.S. Appl. No. 13/725,030, Preliminary Amendment filed Dec. 21, 2012", 6 pgs.

(56) References Cited

OTHER PUBLICATIONS

"U.S. Appl. No. 13/725,030, Restriction Requirement dated Apr. 5, 2013", 9 pgs.
"Australian Application Serial No. 2006282783, First Examiner Report dated Sep. 23, 2011", 3 pgs.
"Australian Application Serial No. 2006282783, Response filed Apr. 12, 2012 to First Examiners Report dated Sep. 23, 2011", 21 pgs.
"Australian Application Serial No. 2006282783, Response filed Apr. 18, 2013 to Subsequent Examiners Report dated May 28, 2012", 5 pgs.
"Australian Application Serial No. 2006282783, Subsequent Examiners Report dated May 28, 2012", 2 pgs.
"Authorized Officer John Shaw, Invitation to Respond to Written Opinion/ Australian Patent Office Written Opinion/ Australian Patent Office Search Report, Singapore Application No. 200801197-5, dated Apr. 2, 2009", 12 pgs.
"Canadian Application Serial No. 2,618,731, Office Action dated Mar. 27, 2013", 3 pgs.
"Chinese Application Serial No. 200680030925.4, First Office Action dated Jan. 2, 2010", (English Translation), 4 pgs.
"Chinese Application Serial No. 200680030925.4, Office Action dated Sep. 28, 2011", (w/ English Translation), 10 pgs.
"Chinese Application Serial No. 200680030925.4, Response filed Apr. 15, 2011 to Office Action dated Jan. 31, 2011", (w/ English Translation of Amended Claims), 9 pgs.
"Chinese Application Serial No. 200680030925.4, Response Filed Oct. 19, 2010 to Office Action dated Jun. 4, 2010", (w/ English Translation of Claims), 10 pgs.
"Chinese Application Serial No. 200680030925.4, Response filed Oct. 19, 2010 to Second Office Action dated Jun. 4, 2010", (w/ English Translation of Amended Claims), 10 pgs.
"Chinese Application Serial No. 200680030925.4, Response filed Dec. 12, 2011 to Office Action daed Sep. 28, 2011", 4 pgs.
"Chinese Application Serial No. 200680030925.4, Second Office Action dated Jun. 4, 2010", (w/ English Translation), 8 pgs.
"Chinese Application Serial No. 200680030925.4, Third Office Action dated Jan. 31, 2011", (w/ English Translation), 15 pgs.
"Chinese Application Serial No. 201080024899.0, Office Action dated Jan. 9, 2013", 16 pgs.
"European Application Serial No. 06790024.1, Office Action dated Sep. 10, 2010", 7 pgs.
"European Application Serial No. 06790024.1, Response filed Jan. 20, 2011 to Office Action dated Sep. 10, 2010", 11 pgs.
"European Application Serial No. 06790024.1, Supplementary European Search Report dated Jun. 5, 2009", 9 pgs.
"European Application Serial No. 10723848.7, Office Action dated Dec. 2, 2011", 2 pgs.
"European Application Serial No. 11181797.9—Exam Notification Art. 94(3) Received", 3 pgs.
"European Application Serial No. 11181797.9, Extended Search Report dated Jun. 11, 2012", 7 pgs.
"European Application Serial No. 11181797.9, Office Action Response filed Dec. 23, 2011", 5 pgs.
"European Application Serial No. 11181797.9, Response filed Jan. 11, 2013 to Extended European Search Report dated Jun. 11, 2012", 4 pgs.
"Supplementary European Search Report, EP Application No. 06 79 0024, dated May 6, 2009", 6 pgs.
"International Application No. PCT/US/2011/050266, International Search Report dated Jan. 23, 2012", 6 pgs.
"International Application No. PCT/US/2011/050266, International Written Opinion dated Jan. 23, 2012", 8 pgs.
"International Application Serial No. PCT/US2006/033415, International Search Report dated Dec. 21, 2006", 3 pgs.
"International Application Serial No. PCT/US2006/033415, Written Opinion dated Dec. 21, 2006", 4 pgs.
"International Application Serial No. PCT/US2010/029463, International Preliminary Report on Patentability dated Oct. 13, 2011", 8 pgs.

"International Application Serial No. PCT/US2010/029463, International Search Report dated Dec. 20, 2010", 5 pgs.
"International Application Serial No. PCT/US2010/029463, Written Opinion dated Dec. 20, 2010", 8 pgs.
"International Application Serial No. PCT/US2010/046644, Internatiional Search Report dated Jun. 22, 2011", 6 pgs.
"International Application Serial No. PCT/US2010/046644, International Preliminary Report on Patentability dated Mar. 8, 2012", 8 pgs.
"International Application Serial No. PCT/US2010/046644, Written Opinion dated Jun. 22, 2011", 7 pgs.
"International Application Serial No. PCT/US2011/050266, International Preliminary Report on Patentability dated Mar. 5, 2013", 9 pgs.
"Israel Application Serial No. 215463, Notification Prior to Examination dated Nov. 19, 2012", 3 pgs.
"Israeli Application Serial No. 189418, Office Action dated Oct. 5, 2011", 1 pg.
"Israeli Application Serial No. 189418, Office Action dated Apr. 7, 2013", (English Translation), 2 pgs.
"Israeli Application Serial No. 189418, Office Action dated May 17, 2010", (English Translation), 1 pg.
"Israeli Application Serial No. 189418, Office Action Response filed Mar. 19, 2012", With English Translation Only, 9 pgs.
"Israeli Application Serial No. 189418, Response filed Sep. 14, 2010 to Office Action dated May 17, 2010", (English Translation), 5 pgs.
"Japanese Application Serial No. 2008-528231—Office Action Response", 18 pgs.
"Japanese Application Serial No. 2008-528231, Decision of Rejection dated Feb. 4, 2013", 4 pgs.
"Japanese Application Serial No. 2008-528231, Office Action dated May 10, 2012", With English Translation, 8 pgs.
"Korean Application Serial No. 10-2008-7007151, Notice of Preliminary Rejection dated Nov. 24, 2012", 9 pgs.
"Korean Application Serial No. 10-2008-7007151, Response filed Jan. 24, 2012 to Notice of Preliminary Rejection dated Nov. 24, 2012", (w/ English Translation of Claims), 18 pgs.
"Mexican Application Serial No. MX/A/2011/010197, Office Action dated Aug. 31, 2012", (w/ English Summary), 3 pgs.
"Mexican Application Serial No. MX/A/2011/010197, Response filed Dec. 19, 2012 to Office Action dated Aug. 31, 2012", 8 pgs.
"Russian Application Serial No. 2008111503, Office Action dated Sep. 15, 2011", 4 pgs.
"Russian Application Serial No. 2008111503, Office Action dated Oct. 27, 2011", W/ English Translation, 10 pgs.
"Russian Application Serial No. 2008111503, Official Action dated Jul. 12, 2010", (w/ English Translation), 10 pgs.
"Russian Application Serial No. 2008111503, Response Filed Jan. 16, 2012 to Office Action dated Sep. 15, 2011", (w/ English Translation of Amended Claims), 10 pgs.
"Russian Application Serial No. 2008111503, Response filed Jul. 14, 2011 to Official Action dated Jul. 12, 2010", (w/ English Translation of Amended Claims), 18 pgs.
"Russian Application Serial No. 2008111503, Response filed Jul. 15, 2011 to Official Action dated Jul. 12, 2010", (w/ English Translation of Amended Claims), 18 pgs.
"Singapore Application Serial No. 200801197-5, Examination Report dated Sep. 16, 2010", 8 pgs.
"Singapore Application Serial No. 200801197-5, Invitation to Respond to Written Opinion dated Apr. 2, 2009", 12 pgs.
"Singapore Application Serial No. 200801197-5, Response filed Sep. 2, 2009 to Written Opinion dated Apr. 2, 2009", 4 pgs.
"Singaporian Application Serial No. SG 200801197-5, Examination Report dated Aug. 6, 2010", 5 pgs.
Atala, "Recent developments in tissue engineering and regenerative medicine", Curr. Opin. Pediatr. vol. 18, (2006), 167-171.
Atala, et al., "Tissue-engineered autologous bladders for patients needing cystoplasty", Lancet 367, (2006), 1241-1246.
Bader, A., et al., "Tissue engineering of heart valves—human endothelial cell seeding of detergent acellularized porcine valves", Eur J Cardiothorac Surg, 14(3), (1998), 279-284.

(56) References Cited

OTHER PUBLICATIONS

Badylak, "Xenogeneic extracellular matrix as a scaffold for tissue reconstruction", Transpl. Immunol. 12, (2004), 367-377.
Baertschiger and Buhler, et al., "Xenotransplantation Literature Update Nov.-Dec. 2005", Xenotransplantation 13, (2006), 96-99.
Baptista, et al., "A Novel Acellular Biologically Derived Scaffold for Tissue Engineering", [online] Pittsburgh Tissue Engineering Initiative, 2005, [retrieved on Jul. 27, 2005] Retrieved from the Internet: <URL: www.regenerate-online.com/abstract_Baptista. html>.
Baptista, P. M, et al., "The use of whole organ decellularization for the generation of a vascularized liver organoid.", Hepatology, 53(2), (Feb. 2011), 604-17.
Baptista, Pedro, et al., "A Novel Whole Organ Bioscaffold for Tissue Engineering and Regenerative Medicine Applications", The FASEB Journal, 21 (Meeting Abstract Supplement), Database Biosis Abstract, (2007), A1233.
Bodnar, et al., "Damage of Porcine Aortic Valve Tissue Caused by the Surfactant Sodiumdodecylsulphate", Thorac. cardiovasc. Surg. 34, (1986), 82-85.
Borschel, et al., "Contractile Skeletal Muscle Tissue-Engineered on an Acellular Scaffold", Plast. Reconstr. Surg. 113, (2004), 595-602.
Brendel, Klaus, et al., "The acellular perfused kidney: a model for basement membrane permeability", Biology and Chemistry of Basement Membranes, Nicholas A Kefalides, author; New York : Academic Press, (1978), 177-193.
Cartmell and Dunn, "Development of Cell-Seeded Patellar Tendon Allografts for Anterior Cruciate Ligament Reconstruction", Tissue Eng. 10, (2004), 1065-1075.
Cebotari, et al., "Construction of Autologous Human Heart Valves Based on an Acellular Allograft Matrix", Circulation 106 (suppl 1), (2002), I-63-I-68.
Chen, et al., "Acellular collagen matrix as a possible "off the shelf" biomaterial for urethral repair", Urology 54, (1999), 407-410.
Chen, et al., "Experimental and clinical experience using tissue regeneration for urethral reconstruction", World J. Urol. 18, (2000), 67-70.
Chen, et al., "Process development of an acellular dermal matrix (ADM) for biomedical applications", Biomaterials 25, (2004), 2679-2686.
Conconi, et al., "Homologous muscle acellular matrix seeded with autologous myoblasts as a tissue-engineering approach to abdominal wall-defect repair", Biomaterials 26, (2005), 2567-2574.
Courtman, D. W., et al., "Development of a pericardial acellular matrix biomaterial: Biochemical and mechanical effects of cell extraction", J Biomed Materi Res., 28(6), (1994), 655-666.
Crapo, Peter M., et al., "An overview of tissue and whole organ decellularization process", Biomaterials, 32, (2011), 3233-3243.
Dahl, et al., "Decellularized Native and Engineered Arterial Scaffolds for Transplantation", Cell Transplant 12, (2003), 659-666.
Davis and Senger, "Endothelial Extracellular Matrix: Biosynthesis, Remodeling, and Functions During Vascular Morphogenesis and Neovessel Stabilization", Circ. Res. 97, (2005), 1093-1107.
Dellgren, et al., "Eleven years' experience with the Biocor stentless aortic bioprsthesis: clinical and hemodynamic follow-up with long-term relative survival rate", Eur. J. Cardiothorac. Surg. 22, (2002), 912-921.
Den Butter, et al., "Comparison of solutions for preservation of the rabbit liver as tested by isolated perfusion", Transpl. Int 8, (466-471), 1995.
Deng, et al., "Destination Mechanical circulatory Support: Proposal for Clinical Standards", J. Heart Lung Transplant 22, (2003), 365-369.
Deyl, et al., "Physiologia Bohemoslovaca 36(5)", (1987), 425-434.
Elkins, et al., "Decellularized Human Valve Allografts", Ann. Thorac. Surg. 71(suppl 5), (2001), S428-S432.
Engbers-Buijtenhuijs, et al., "Biological characterisation of vascular grafts cultured in a bioreactor", Biomaterials 27, (2006), 2390-2397.
Eshenhagen and Zimmerman, "Engineering Myocardial Tissue", Circ. Res. 97, (2005), 1220-1231.

Firth, et al., "Sodium handling in the isolated perfused kidney of the cirrhotic rat", Clin. Sci. 77(6), (1989), 657-661.
Furuta, et al., "Pulsatile Cardiac Tissue Grafts Using a Novel Three-Dimensional Cell Sheet Manipulation Technique Functionally Integrates With the Host Heart, in Vivo", Circ. Res. 98, (2006), 705-712.
Gerecht-Nir, et al., "Biophysical regulation during cardiac development and application to tissue engineering", Int. J. Dev. biol. 50, (2006), 233-243.
Gilbert, et al., "Decellularization of tissues and organs", Biomaterials 27, (2006), 3675-3683.
Gilbert, Thomas W., et al., "Decellularization of tissues and organs", Biomaterials, 27, (2006), 3675-3683.
Grabow, et al., "Mechanical and Structural Properties of a Novel hybrid heart Valve Scaffold for Tissue Engineering", Artif. Organs 28(11), (2004), 971-979.
Groetzner, et al., "Results of Pediatric Cardiac Transplantation—Long-Term Results of a 15-Year Experience", Thorac. Cardiov. Surg 53 (Suppl 2), (2005), S149-S154.
Hohlfeld, et al., "Tissue engineered fetal skin constructs for paediatric burns", Lancet 366, (2005), 840-842.
Hopper, "Ann Plast Surg 51", (2003), 598-602.
Hou, et al., "Tissue-engineered peripheral nerve grafting by differentiated bone marrow stromal cells", Neuroscience 140, (2006), 101-110.
Hudson, et al., "Engineering an Improved Acellular Nerve Graft via Optimized Chemical Processing", Tissue Eng. 10, (2004), 1346-1358.
Ikeda, et al., "Growing bioengineered teeth from single cells: potential for dental regenerative medicine", Expert Opin. Biol. Ther. 8(6), (2008), 735-744.
Isenberg, et al., "Small Diameter Artificial Arteries Engineered In Vitro", Circ. Res. 98, (2006), 25-35.
Jawad, et al., "Myocardial Tissue Engineering", British Medical Bulletin 87, (2008), 31-47.
Juncosa-Melvin, et al., "The Effect of Autologous Mesenchymal Stem Cells on the Biomechanics and Histology of Gel-Collagen Sponge Constructs Used for Rabbit Patellar Tendon Repair", Tissue Eng. 12, (2006), 369-379.
Kasimir, et al., "The decellularized porcine heart valve matrix in tissue engineering. Platelet adhesion and activation", (2005), 562-567.
Ketchedjian, et al., "Recellularization of Decellularized Allograft Scaffolds in Ovine Great Vessel Reconstructions", Ann. Thorac. Surg. 79, (2005), 888-896.
Knight, et al., "Tissue Engineering of Cardiac Valves: Re-Seeding of Acellular Porcine Aortic Valve Matrices with human Mesenchymal Progenitor Cells", J. Heart Valve Dis. 14, (2005), 806-813.
Kofidis, et al., "Myocardial Restoration and Tissue Engineering of Heart Structures", Methods mol. Med. 140, (2007), 273-290.
Kolker, et al., "Multilayer Reconstruction of abdominal Wall defects with Acellular Dermal Allograft (AlloDerm) and component Separation", Ann. Plast. Surg. 55, (2005), 36-41.
Kren, S., "Abstract 580: The Production of a Bio-Engineered Endothelial Intima From Cultured Cells Using Whole Cardiac Caraveric Extracellular Matrix", Circulation, 116, (Abstract Only), (2007), 1 pg.
Kren, Stefan, et al., "The Production of a Bio-Engineered Endothelial Intima From Cultured Cells Using Whole Cardiac Cadaveric Extracellular Matrix", Circulation, 116 (Meeting Abstract Supplement), Database Biosis, (2007), Abstract 580.
Langer, R., et al., "Tissue Engineering", Science, 260, (1993), 920-926.
Lee, "GraftJacket Augmentation of Chronic Achilles Tendon Ruptures", Orthopedics 27, (2004), 151-153.
Levenberg, et al., "Engineering vascularized skeletal muscle tissue", Nat. Biotechnol. 23(7), (2005), 879-884.
L'Heureux, et al., "Human tissue-engineered blood vessels for adult arterial revascularization", Nat. med. 12(3), (2006), 361-365.
Lichtenberg, et al., "Flow-Dependent Re-Endothelialization of Tissue-Engineered Heart Valve", J. Heart Valve Dis. 15, (2006), 287-294.
Lin, et al., "Accessing Porcine Liver-Derived Biomatrix for Hepatic Tissue Engineering", Tissue Eng. 10, (2004), 1046-1053.

(56) References Cited

OTHER PUBLICATIONS

Matsuura, et al., "Cellular Remodeling of Depopulated Bovine Ureter Used as an Arteriovenous Graft in the Canine Model", J. Am Coll Surg. 198(5), (2004), 778-783.

Matthiesen, T. S., et al., "Abstract 572: Large Solid Organ Perfusion Decellularization—A Start for Human-Sized Tissue Scaffolds", Circulation, 116, (2007), 1 pg.

Matthiesen, Thomas, et al., "Creating Biocompatible 3-D Scaffolds for Engineering Cardiovascular Tissues: Heart, Lung, and Kidney", Circulation, 116 (Meeting Abstract Supplement), Database Biosis, (Oct. 2007), Abstract 428.

Matthiesen, Thomas S, et al., "Large Solid Organ Perfusion Decellularization—A Start for Human-Sized Tissue Scaffolds?", Circulation, 116 (Meeting Abstract Supplement), Database Biosis, (Oct. 2007), Abstract 572.

Mazzetti, et al., "Molecular anatomy of the cerebral microvessels in the isolated guinea-pig brain", Brain Res. 999, (2004), 81-90.

McFetridge, et al., "Preparation of porcine carotid arteries for vascular tissue engineering applications", J. Biomed. Mater Res. A 70A, (2004), 224-234.

Mirsadraee, et al., "Development and Characterization of an Acellular Human Pericardial matrix for Tissue Engineering", Tissue Eng. 12(4), (2006), 763-773.

Miyagawa, et al., "Tissue Cardiomyoplasty using bioengineered Contractile Cardiomyocyte Sheets to Repair Damaged Myocardium: Their Integration with Recipient Myocardium", Transplantation, 80(11), (2005), 1586-1595.

Nikalson, et al., "Functional Arteries Grown in Vitro", Science 284, (1999), 489-493.

Oliver, et al., "Dermal Collagen Implants", Biomaterials 1, (1982), 38-40.

Ott, et al., "Perfusion-Decellularized Matrix: Using Nature's Platform to Engineer a Bioartificial Heart", Nat. Med 14(2), (2008), 213-221.

Ott, H. C., et al., "Cell-Based Cardiovascular Repair", Basic Res Cardiol, 100, (2005), 504-517.

Ott, H. C, et al., "Perfusion-decellularized matrix: using nature's platform to engineer a bioartificial heart", Nat Med., 14(2), Database Medline, (Feb. 2008), 213-221.

Ott, H. C, et al., "Perfusion-decellularized matrix: using nature's platform to engineer a bioartificial heart.", Nat Med., 14(2), (Feb. 2008), 213-21.

Ott, H. C, et al., "Regeneration and orthotopic transplantation of a bioartificial lung.", Nature Medicine, Advance Online Publication, (2010), 8 pgs.

Park, et al., "A novel composite scaffold for cardiac tissue engineering", In Vitro Cell Dev. Biol. Anim. 41, (2005), 188-196.

Pelham, Jr., et al., "Cell locomotion and focal adhesions are regulated by substrate flexibility", Proc. Natl. Acad. Sci. USA 94, (1997), 13661-13665.

Peters, J. M., et al., "Organ Weights and Water Levels of the Rat following Reduced Food Intake", The Journal of Nutrition, 90, (1966), 354-360.

Petersen, T. H, et al., "Tissue-engineered lungs for in vivo implantation", Science Express, www.sciencexpress.org, (Jun. 24, 2010), 10 pgs.

Phillips, et al., "Neural Tissue Engineering: A Self-Organizing Collagen Guidance Conduit", Tissue Eng. 11, (2005), 1611-1617.

Powers, et al., "Functional Behavior of Primary Rat Liver Cells in a Three-Dimensional Perfused Microarray Bioreactor", Tissue Eng. 8(3), (2002), 499-513.

Radisic, M., et al., "Mathematical model of oxygen distribution in engineered cardiac tissue with parallel channel array perfused with culture medium containing oxygen carriers.", Am J Physiol Heart Circ Physiol., 288(3), (Mar. 2005), H1278-89.

Rieder, et al., "Decellularization protocols of porcine heart valves differ importantly in efficiency of cell removal and susceptibility of the matrix to recellularization with human vascular cells", J. Thorac. Cardiovasc. Surg. 127, (2004), 399-405.

Rieder, E., et al., "Decellularization protocols of porcine heart valves differ importantly in efficiency of cell removal and susceptibility of the matrix to recellularization with human vascular cells.", J Thorac Cardiovasc Surg., 127(2), (Feb. 2004), 399-405.

Robinson, et al., "Extracellular Matrix Scaffold for Cardiac Repair", Circulation 112[suppl I], (2005), I-135-I-143.

Roy, et al., "Biomechanical properties of decellularized porcine common carotid arteries", Am. J. Physiol. Heart Circ. Physiol. 289, (2005), H1567-H1576.

Sayk, et al., "Histopathologic Findings in a Novel Decellularized Pulmonary Homograft: An Autopsy Study", Ann. Thorac. Surg 79(5), (2005), 1755-1758.

Schaner, P. J, et al., "Decellularized vein as a potential scaffold for vascular tissue engineering", J Vasc Surg., 40(1), (Jul. 2004), 146-53.

Schenke-Layland, et al., "Complete Dynamic Repopulation of Decellularized Heart Valves by Application of Defined Physical Signals—an in Vitro Study", Cardiovasc. Res. 60(3), (2003), 497-509.

Schenke-Layland, K., et al., "Complete dynamic repopulation of decellularized heart valves by application of defined physical signals—an in vitro study.", Cardiovasc Res., 60(3), (Dec. 1, 2003), 497-509.

Schenke-Layland, K., et al., "Impact of decellularization of xenogeneic tissue on extracellular matrix integrity for tissue engineering of heart valves", J. Struct. Biol., 143, (2003), 201-208.

Schlager, Gunther, "Kidney Weight in Mice: Strain Differences and Genetic Determinatino", The Journal of Heredity, 59, (1968), 171-174.

Schmidt, C. E, et al., "Acellular vascular tissues: natural biomaterials for tissue repair and tissue engineering", Biomaterials, 21(22), (Nov. 2000), 2215-31.

Sekine, et al., "Cardiomyocyte Bridging Between Hearts and Bioengineered Myocardial Tissues with Mesenchymal Transition of Mesothelial Cells", J. Heart Lung Transplant 25, (2006), 324-332.

Shimizu, T., et al., "Fabrication of pulsatile cardiac tissue grafts using a novel 3-dimensional cell sheet manipulation technique and temperature-responsive cell culture surfaces.", Circ Res., 90(3), (Feb. 22, 2002), e40-e48.

Shyy, et al., "Role of Integrins in Endothelial Mechanosensing of Shear Stress", Circ. Res. 91, (2002), 769-775.

Stevenson, et al., "Left Ventricular Assist Device as Destination for Patients Undergoing Intravenous Inotropic Therapy. A Subset Analysis from REMATCH (Randomized Evaluation of Mechanical Assistance in Treatment of Chronic Heart Failure)", Circulation 110, (2004), 975-981.

Sudo, et al., "Reconstruction of 3d stacked-up structures by rat small hepatocytes on microporous membranes", FASEB J. 19, (2005), 1695-1697.

Sun, et al., "Development of a Closed Bioreactor System for Culture of Tissue-Engineered Skin at an Air-Liquid Interface", Tissue Eng. 11, (2005), 1824-1831.

Takagi, et al., "In Vivo Recellularization of Plain Decellularized Xenografts with Specific Cell Characterization in the Systemic Circulation: Histological and Immunohistochemical Study", Artif. Organs 30(4), (2006), 233-241.

Taylor, Doris A, et al., "Regenerating Functional Myocardium: Improved Performance after Skeletal Myoblast Transplantation", Nature Medicine, 4(8), (1998), 929-933.

Teebken, et al., "Tissue engineering of vascular grafts: human cell seeding of decellularised porcine matrix", Eur. J. Vasc. Endovasc. Surg 19, (2000), 381-386.

Teebken, O. E, et al., "Tissue engineering:in vitro creation of tissue substitutes", Zentralbl Chir.,132(3), (2007), 236-246.

Toni, et al., "The Bioartifical Thyroid: a Biotechnical Perspective in Endocrine Organ Engineering for Transplantation Replacement", Acta biomed. 78(Suppl 1), (2007), 129-155.

Uchimura, et al., "Novel method of preparing acellular cardiovascular grafts by decellularization with poly(ethylene glycol)", J. Biomed. Mater. Res. 67A, (2003), 834-837.

Uygun, B. E, et al., "Organ reengineering through development of a transplantable recellularized liver graft using decellularized liver matrix.", Nature Medicine, Advance Online Publication, (2010), 8 pgs.

(56) References Cited

OTHER PUBLICATIONS

Wagner, et al., "The isolated normothermic hemoperfused porcine forelimb as a test system for transdermal absoption studies", J Artif. Organs 6(3), (2003), 183-191.
Walles, et al., "Acellular Scaffold Implantation—No Alternative to Tissue Engineering", Int. J. Artif. Organs 26(3), (2003), 225-234.
Wang, et al., "Reconstruction of Renal Glomerular Tissue Using Collagen Vitrigel Scaffold", J. biosci. bioeng. 99(6), (2005), 529-540.
Woods, et al., "Effectiveness of three extraction techniques in the development of a decellularized bone-anterior cruciate ligament-bone graft", Biomaterials, Elsevier Science Publishers, vol. 26, No. 35, (Dec. 1, 2005), 7339-7349.
Zandonella, "Tissue Engineering: The Beat Goes on", Nature 421, (2003), 884-886.
Zeltinger, et al., "Development and characterization of Tissue-Engineered Aortic Valves", Tissue Engineering 7, (2001), 9-22.
Zimmermann, et al., "Engineered heart tissue grafts improve systolic and diastolic function in infarcted rat hearts", Nat. med. 12(4), (2006), 452-458.
Zimmermann, W. H, et al., "Engineered heart tissue for regeneration of diseased hearts", Biomaterials, 25(9), (Apr. 2004), 1639-47.
"U.S. Appl. No. 13/913,974, Declaration of Dr. Jeffrey Ross filed Feb. 24, 2016", 5 pgs.
"U.S. Appl. No. 12/064,613, Declaration of Dr. Doris Taylor filed Jan. 26, 2012", 4 pgs.
"U.S. Appl. No. 12/064,613, Declaration of Dr. Jeffrey Ross filed Mar. 4, 2013", 8 pgs.
"U.S. Appl. No. 13/262,286, Response filed Dec. 7, 2015 to Final Office Action dated Jun. 11, 2015", 8 pgs.
"U.S. Appl. No. 13/725,030, Examiner Interview Summary dated Jan. 22, 2015", 4 pgs.
"U.S. Appl. No. 13/725,030, Examiner Interview Summary dated Jan. 29, 2016", 5 pgs.
"U.S. Appl. No. 13/725,030, Examiner Interview Summary dated Jun. 29, 2015", 3 pgs.
"U.S. Appl. No. 13/725,030, Non Final Office Action dated Oct. 2, 2015", 31 pgs.
"U.S. Appl. No. 13/725,030, Response filed Aug. 25, 2015 to Final Office Action dated May 19, 2015", 21 pgs.
"U.S. Appl. No. 13/820,079, Advisory Action dated Aug. 13, 2015", 3 pgs.
"U.S. Appl. No. 13/820,079, Examiner Interview Summary dated Sep. 28, 2015", 3 pgs.
"U.S. Appl. No. 13/820,079, Response filed Sep. 23, 2015 to Final Office Action dated Apr. 23, 2015", 10 pgs.
"Canadian Application Serial No. 2,618,731, Office Action dated Jan. 5, 2016", 4 pgs.
"Canadian Application Serial No. 2,618,731, Response filed Dec. 12, 2014 to Office Action dated Jun. 13, 2014", 28 pgs.
"European Application Serial No. 15170077.0, Extended European Search Report dated Dec. 7, 2015", 12 pgs.
"European Application Serial No. 15170077.0, Response filed Aug. 21, 2015 to Office Action dated Jun. 12, 2015", 4 pgs.
"Israel Application Serial No. 233821, Office Action dated Jul. 7, 2015", (English Translation), 2 pgs.
"Stem Cell Definition", [online]. [retrieved on Sep. 21, 2015]. Printout from <www.google.com/search?q=%22stem+cell%22+definition&sourceid=ie7&rls=com.micorsoft.en.>, (2015), 1-2.
Brodie, T. G., "The perfusion of surviving organs", The Journal of Physiology, 29(3), (Jan. 1, 1903), 266-275.
Czyz, Jaroslaw, et al., "Embryonic stem cell differentiation: The role of extracellular factors", Differentiation, 68, (2001), 167-174.
Downing, Gregory J., et al., "Technical Assessment of the First 20 Years of Research Using Mouse Embryonic Stem Cell Lines", Stem Cells, 22, (2004), 1168-1180.
Keller, Gorder, "Embryonic stem cell differentiation: emergence of a new era in biology and medicine", Genes & Development, 19, (2005), 1129-1155.

Lu, Tung-Ying, et al., "Repopulation of decellularized mouse heart with human induced pluripotent stern cell-derived cardiovascular progenitor cells", Nature Communications, 4, (2013), 1-11.
Munoz-Elias, Guillermo, et al., "Marrow Stromal Cells, Mitosis, and Neuronal Differentiation: Stem Cell and Precursor Functions", Stem Cells, 21(4), (Jul. 2003), 437-448.
Oswald, Joachim, et al., "Mesenchymal Stem Cells can be Differentiated Into Endothelial Cells In Vitro", Stem Cells, 22(3), (204), 377-384.
Ross, Edward A, et al., "Embryonic Stem Cells Proliferate and Differentiate when Seeded into Kidney Scaffolds", Journal of the American Society of Nephrology, vol. 20, No. 11, (2009), 2338-2347.
Ross, Edward A., et al., "Mouse stem cells seeded into decellularized rat kidney scaffolds endothelialize and remodel basement membranes", Organogenesis, 8:2, (2012), 49-55.
Song, Jeremy J,, et al., "Organ engineering based on decellularized matrix scaffolds", Trends in Molecular Medicine 17(8), (2012), 424-432.
Swanson, Julia C., et al., "Characterization of Mitral Valve Anterior Leaflet Perfusion Paterns", NIH Public Access, published in final edited form as: J. Heart Valve Dis., 18(5), (2009), 488-495.
Yang, Lijun, et al., "In vitro trans-differentiation of adult hepatic stem cells into pancreatic endocrine hormone-producing cells", Proc. Natl. Acad. Sci. USA, 99(12), (2002), 8078-8083.
"U.S. Appl. No. 13/262,286, Non Final Office Action dated Jun. 10, 2016", 8 pgs.
"U.S. Appl. No. 13/725,030, Final Office Action dated Jun. 23, 2016", 26 pgs.
"U.S. Appl. No. 13/425,030, Response filed Apr. 1, 2016 to Non Final Office Action dated Oct. 2, 2015", 23 pgs.
"U.S. Appl. No. 13/820,079, Non Final Office Action dated May 31, 2016", 15 pgs.
"U.S. Appl. No. 13/820,079, Response filed Aug. 30, 2016 to Non Final Office Action dated May 31, 2016", 8 pgs.
"Canadian Application Serial No. 2,618,731, Response filed Jul. 4, 2016 to Office Action dated Jan. 5, 2016", 4 pgs.
"Israel Application Serial No. 233821, Response filed Apr. 10, 2016 to Office Action dated Jul. 7, 2015", 5 pgs.
"Japanese Application Serial No. 2015-094591, Office Action dated Apr. 13, 2016", 1 pg.
Batchelder, Cynthia A., et al., "Natural Scaffolds for Renal Differentiation of Human Human Embryonic Stem Cells for Kidney Tissue Engineering", PLOS One, 10(12): e0143849, (2015), 18 pgs.
Duhaut, Susan, et al,, "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Guan, Yong, et al., "The effective bioengineering method of implantation decellularized renal extracellular matrix scaffolds", Oncotarget,6(34), (2015), 36126-36138.
Hussein, Kamal H., "Three dimensional culture of HepG2 liver cells on a rat decellurized liver matrix for pharmacological studies", Journal of Biomedical Materials B: Applied Biomaterials, vol. 104B, Issue 2, (2015), 263-273.
Kitahara, Hiroto, et al., "Heterotopic transplantation of a decellularized and recellularized whole porcine heart", Interactive Cardiovascular and Thoracic Surgery, (2016), 1-9.
Navarro-Tableros, Victor, et al., "Recellularization of Rat Liver Scaffolds by Human Liver Stern Ceils", Tissue Engineering: Part A, vol. 21, Nos. 11 and 12, (2015), 1929-1939.
Uzarski, Joseph S., et al., "Epithelial Cell Repopulation and Preparation of Rodent Extracellular Matrix Scaffolds for Renal Tissue Development", Journal of Visualized Experiments, e53271, (2015), 9 pgs.
Wang, Xiaojun, et al., "Decellularized liver scaffolds effectively support the proliferation and differentiation of mouse fetal hepatic progenitors", J. Biomed Mater Res Part A, 102A, (2014), 2027-2025.
Zhou, Pengcheng, et al., "Decellularization and Recellularization of Rat Livers With Hepatocytes and Endothelial Progenitor Cells", Artificial Organs, (2015), 1-14.

(56) References Cited

OTHER PUBLICATIONS

"U.S. Appl. No. 13/262,286, Final Office Action dated Mar. 9, 2017", 7 pgs.
"U.S. Appl. No. 13/262,286, Response filed Dec. 8, 2016 to Non Final Office Action dated Jun. 10, 2016", 7 pgs.
"U.S. Appl. No. 13/725,030, Non Final Office Action dated Jan. 6, 2017", 28 pgs.
"U.S. Appl. No. 13/725,030, Response filed Nov. 23, 2016 to Final Office Action dated Jun. 23, 2016", 14 pgs.
"U.S. Appl. No. 13/725,030, Response Filed Nov. 23, 2016 Final Office Action dated Jun. 23, 2016", 14 pgs.
"U.S. Appl. No. 13/820,079, Final Office Action dated Nov. 21, 2016", 16 pgs.
"Australian Application Serial No. 2015224503, First Examiner Report dated Dec. 5, 2016", 4 pgs.
"Australian Application Serial No. 2015224503, First Examiner Report dated Dec. 5, 2016", 14 pgs.
"Australian Application Serial No. 2015224503, Subsequent Examiners Report dated May 4, 2017", 4 pgs.
"Canadian Application Serial No. 2,618,731, Office Action dated Apr. 7, 2017", 5 pgs.
"European Application Serial No. 15170077.0, Communication Pursuant to Article 94(3) EPC dated Feb. 1, 2017", 2 pgs.
"Japanese Application Serial No. 2015-094591, Office Action dated Apr. 13, 2016", (w/ English Translation), 10 pgs.
"Japanese Application Serial No. 2015-094591, Written Argument and Amendment filed Oct. 13, 2016 to Office Action dated Apr. 13, 2016", (w/ English Translation of Claims), 21 pgs.
"Liver Regeneration", [online]. (c) 1998-2016 Mayo Foundation for Medical Education and Research, Retrieved from the Internet: <URL: http://www.mayo.edu/research/centers-programs/center-regenerative-medicine/focus-areas/liver-regeneration>, (2016), 2 pgs.
"Mexican Application Serial No. MX/a/2014/006778, Office Action dated Jan. 30, 2017", (w/ English Translation), 4 pgs.
"Mexican Application Serial No. MX/a/2014/006778, Office Action dated Sep. 14, 2016", (w/ English Summary), 3 pgs.
"Russian Application Serial No. 2012122055, Office Action dated Mar. 9, 2017", (w/ English Translation), 7 pgs.
"Russian Application Serial No. 2012122055, Office Action dated Jul. 11, 2016", (With English Translation), 13 pgs.
"Russian Application Serial No. 2012122055, Response filed Jan. 11, 2017 to Office Action dated Jul. 11, 2016", (w/ English Summary), 4 pgs.
Lapidot, Tsvee, et al., "How do stem cells find their way home?", Blood, 106(6), (2005), 1901-1910.
Perry, Robert, et al., "Clinical Scale Expansion of Human Pluripotent Stem Cells", (Abstract Only), Blood, 106(11), (2005), 1 pg.
Philp, D., et al., "Complex extracellular matrices promote tissue-specific stem cell differentiation.", (Abstract Only), Stem Cells, 23(2), 288-296, (2005), 1.
"U.S. Appl. No. 13/820,079, Response filed May 18, 2017 to Final Office Action dated Nov. 21, 2016", 11 pgs.
"Australian Application Serial No. 2015224503, Resoonse filed Apr. 5, 2017 to First Examiner Report dated Dec. 5, 2016", 14 pgs.
Weind, Kirsten L., et al., "The Aortic Valve Blood Supply", *J. Heart Valve Dis.*, 9(1), (Jan. 2000), 1-8.
"U.S. Appl. No. 13/262,286, Advisory Action dated Jun. 27, 2017", 3 pgs.
"U.S. Appl. No. 13/262,286, Response filed Jun. 9, 2017 to Final Office Action dated Mar. 9, 2017", 8 pgs.
"U.S. Appl. No. 13/725,030, Final Office Action dated Sep. 13, 2017", 20 pgs.
"U.S. Appl. No. 13/725,030, Response filed Jul. 6, 2017 to Non Final Office Action dated Jan. 6, 2017", 16 pgs.
"U.S. Appl. No. 13/725,030, Response Filed Dec. 12, 2017 to Final Office Action dated Sep. 13, 2017", 17 pgs.
"U.S. Appl. No. 13/820,079, Non Final Office Action dated Nov. 1, 2017", 18 pgs.

"Australian Application Serial No. 2015224503, Response filed Oct. 9, 2017 to Subsequent Examiners Report dated May 4, 2017", 24 pgs.
"Australian Application Serial No. 2015224503, Response filed Nov. 16, 2017 to Subsequent Examiners Report dated Nov. 7, 2017", 177 pgs.
"Australian Application Serial No. 2015224503, Subsequent Examiners Report dated Nov. 7, 2017", 3 pgs.
"Australian Application Serial No. 2015224503, Subsequent Examiners Report dated Nov. 22, 2017", 3 pgs.
"Australian Application Serial No. 2015224503, Subsequent Examiners Report dated Dec. 5, 2017", 3 pgs.
"Canadian Application Serial No. 2,618,731, Response filed Sep. 26, 2017 to Office Action dated Apr. 7, 2017", 65 pgs.
"European Application Serial No. 15170077.0, Communication Pursuant to Article 94(3) EPC dated Oct. 24, 2017", 2 pgs.
"European Application Serial No. 15170077.0, Response filed Aug. 11, 2017 to Communication Pursuant to Article 94(3) EPC dated Feb. 1, 2017", 10 pgs.
"Japanese Application Serial No. 2016-201559, Office Action dated Nov. 8, 2017", W/ English Translation, 6 pgs.
"Mexican Application Serial No. MX/a/2014/006778, Response filed Jun. 5, 2017 to Office Action dated Jan. 30, 2017", (w/ English Translation of Claims), 14 pgs.
"Russian Application Serial No. 2012122055, Official Decision of Grant dated Jul. 13, 2017", (w/ English Translation), 14 pgs.
"Russian Application Serial No. 2012122055, Response filed Jun. 8, 2017", (w / English Translation of Claims), 14 pgs.
Badylak, SF, "Xenogeneic extracellular matrix as a scaffold for tissue reconstruction", Trnaspl Immunol. Apr. 2004;12(3-4):367-77, 2.
Frantz, Christian, et al., "The extracellular matrix at a glance", Cell Science at a Glance 123, (2010), 4195-4200.
Fridman, Robert, et al., "A Pilot Study to Evaluate the Effects of Perfusion-decellularized Porcine Hepatic-derived Wound Matrix on Difficult-to-heal Diabetic Foot Ulcers", The official journal of AAWC, WOUNDS, A Compendium of Clinical Research and Practice, vol. 29, No. 10, Oct. 2017, (2017), 317-324.
Naito, H., et al., "Tjhree-dimensinal cardiac tissue engineering using a thermorespoonsive artificial extracellular matrix", ASAIO J. Jul.-Aug. 2004; 50(4):344-8, (2017), 2.
Park, JK, et al., "Bioartificial liver systems: current status and future perspective", J Biosci Bioeng. Apr. 2005;99(4):311-9, (2005), 2.
Petro, Clayton C., et al., "An in vivo analysis of Miromesh—a novel porcine liver prosthetic created by perfusion decellularization", Journal of Surgical Resarch 201, (2016), 29-37.
Saito, A., "Development of bioartificial kidneys", Nephrology (Carlton). Oct. 8, 2003 Suppl:S10-5, (2003), 1.
Sarraf, CE, et al., "Cell proliferation rates in an artifical tissue-engineered environment", Cell Prolif. Aug. 2005;38(4):215-21, (2005), 2.
Stocum, DL, "Regenerative biology and medicine", J. Musculoskelet Neuronal Interact. Mar. 2002;2(3):270-3, (2002), 2.
Wang, X, et al., "Preparation and characterization of a collagen/chitosan/heparin matrix for an implantable bioartificial liver", J Biomater Sci Polym Ed. 2005;16(9):1063-80, (2005), 2.
JP2008-528231 Response dated Nov. 12, 2012 (with English translation).
U.S. Appl. No. 13/725,030 Examiner Interview Summary dated Jun. 25, 2018.
U.S. Appl. No. 13/725,030 Examiner Interview Summary dated May 6, 2014.
U.S. Appl. No. 13/725,030 Office Action dated Jan. 29, 2018.
Robinson, et al. Extracellular matrix scaffold for cardiac repair. Circulation. Aug. 30, 2005;112(9 Suppl):I135-43.
U.S. Appl. No. 13/820,079 Notice of Allowance dated Oct. 29, 2018.
AU2010236855 First Amendment dated Aug. 6, 2014.
AU2010236855 First Examiner Report dated Jan. 17, 2014.
AU2011295779 Examination Report dated Jan. 30, 2015.
AU2011295779 Response dated Aug. 3, 2015.

(56) References Cited

OTHER PUBLICATIONS

Badylak et al. Whole-organ tissue engineering: decellularization and recellularization of three-dimensional matrix scaffolds. Annu Rev Biomed Eng., 13, (2011), 27-53.
CA2757457 Office Action dated Dec. 29, 2016.
CA2757457 Office Action dated Feb. 26, 2016.
CA2757457 Office Action Response dated Jun. 28, 2017.
CA2757457 Response dated Aug. 26, 2016.
CA2809990 Office Action dated Nov. 27, 2017.
CN201180052952.2 Office Action dated Apr. 17, 2014.
CN201180052952.2 Office Action dated Dec. 18, 2014 (w/ English Translation).
CN201180052952.2 Office Action dated May 15, 2015 (w/ English Translation).
CN201180052952.2 Office Action dated Oct. 19, 2015 (w / English Translation).
CN201180052952.2 Response dated Dec. 24, 2015.
CN201180052952.2 Response dated Feb. 27, 2015 (w/ English Translation of Claims).
CN201180052952.2 Response dated Jul. 30, 2015 (w/ English Translation of Amended Claims).
CN201180052952.2 Response dated Sep. 2, 2014 (WI English Translation of Claims).
EP10723848.7 Office Action dated Jul. 8, 2014.
EP10723848.7 Response dated Jun. 12, 2012.
EP11776927.3 Examination Notification Art. 94(3) dated Feb. 5, 2014.
EP11776927.3 Office Action dated Apr. 23, 2013.
EP11776927.3 Response dated Aug. 15, 2014.
EP11776927.3 Response dated Aug. 15, 2015.
EP11776927.3 Response dated Jul. 2, 2015.
EP11776927.3 Response dated Nov. 4, 2013.
EP11776927.3 Result of Consultation dated Jun. 29, 2015.
IL215463 Office Action dated Oct. 20, 2014 (w/ English Translation).
IL224964 Office Action dated Dec. 20, 2015.
IL224964 Office Action dated Nov. 23, 2016 (w/ English Translation).
IL224964 Response dated Jun. 19, 2016 (w / English Translation).
IL224964 Response dated Nov. 25, 2017.
JP2012-503673 Argument and Amendment dated Nov. 28, 2014 (w/ English Translation).
JP2012-503673 Decision of Rejection dated Apr. 22, 2015 (w/ English Translation).
JP2012-503673 Office Action dated Aug. 28, 2014 (w/ English Translation).
JP2013-527329 Office Action dated Jul. 8, 2015 (w/ English Translation).
JP2013-527329 Response dated Oct. 7, 2015 (W/ English Translation of Written Amendment).
JP2015-164446 Examiners Decision of Final Refusal dated Mar. 30, 2017 (w/ English Translation).
JP2015-164446 Office Action dated Dec. 14, 2016.
JP2015-164446 Office Action dated Jul. 27, 2016 (w / English Translation).
JP2015-164446 Response dated Nov. 21, 2016 (w/ English Translation of Written Amendment and Argument).
JP2015-164446 Written Amended dated Mar. 13, 2017 (w/ English Translation).
Kang et al. Decellularization technology application in which live reconstruct biological scaffold. National Medical Journal of China, vol. 89, No. 16, 1135-1138, (2009).
KR10-2013-7008118 Notice of Preliminary Rejection dated Nov. 20, 2017 (w/ English Translation).
MX/A/2011/010197 Office Action dated Apr. 17, 2013 (w/ English Summary).
MX/A/2011/010197 Response dated Sep. 10, 2013.
MX/a/2013/002372 Substantive Examination Report dated Mar. 17, 2016 (w / English Summary).
PCT/US2006/033415 International Preliminary Report on Patentability dated Feb. 26, 2008.
RU2011143730 Office Action dated Apr. 1, 2014 (w/ English Translation).
RU2011143730 Office Action dated Sep. 19, 2014 (w/ English Translation).
RU2011143730 Response dated Aug. 28, 2014 (w/ English Translation of Claims).
RU2013114382 Office Action dated Nov. 21, 2015 (w/ English Translation).
RU2013114382 Office Action dated Feb. 16, 2016 (w / English Translation).
RU2013114382 Response dated Aug. 16, 2016 (w / English Translation of Amended Claims).
RU2013114382 Response dated Jan. 21, 2016.
U.S. Appl. No. 13/262,286 Response dated Feb. 14, 2014.
U.S. Appl. No. 13/262,286 Response dated Jun. 10, 2013.
U.S. Appl. No. 13/913,974 Response dated Aug. 10, 2015.

DECELLULARIZATION AND RECELLULARIZATION OF SOLID ORGANS

CROSS REFERENCE TO RELATED APPLICATIONS

This application is a continuation of U.S. patent application Ser. No. 13/725,030, filed Dec. 21, 2012, which is a continuation of U.S. patent application Ser. No. 12/064,613, filed Oct. 27, 2008, which is a National Stage application under 35 U.S.C. § 371 and claims benefit under 35 U.S.C. § 119(a) of International Application No. PCT/US2006/033415 having an International Filing Date of Aug. 28, 2006, which claims the benefit of priority of U.S. Application No. 60/815,242 having a filing date of Jun. 19, 2006 and U.S. Application No. 60/711,501 having a filing date of Aug. 26, 2005.

TECHNICAL FIELD

This invention relates to organs and tissues, and more particularly to methods and materials for decellularizing and recellularizing organs and tissues.

BACKGROUND

Biologically derived matrices have been developed for tissue engineering and regeneration. The matrices developed to date, however, generally have a compromised matrix structure and/or do not exhibit a vascular bed that allows for effective reconstitution of the organ or tissue. This disclosure describes methods for decellularization and recellularization of organs and tissues.

SUMMARY

The invention provides for methods and materials to decellularize an organ or tissue as well as methods and materials to recellularize a decellularized organ or tissue.

In one aspect, the invention provides for a decellularized mammalian heart. A decellularized mammalian heart includes a decellularized extracellular matrix of the heart that has an exterior surface. The extracellular matrix of a decellularized heart substantially retains the morphology of the extracellular matrix prior to decellularization, and the exterior surface of the extracellular matrix is substantially intact.

Representative hearts include but are not limited to rodent hearts, pig hearts, rabbit hearts, bovine hearts, sheep hearts, or canine hearts. Another representative heart is a human heart. The decellularized heart can be cadaveric. In some embodiment, the decellularized heart is a portion of an entire heart. For example, a portion of an entire heart can include, without limitation, a cardiac patch, an aortic valve, a mitral valve, a pulmonary valve, a tricuspid valve, a right atrium, a left atrium, a right ventricle, a left ventricle, septum, coronary vasculature, a pulmonary artery, or a pulmonary vein.

In another aspect, the invention provides for a solid organ. A solid organ as described herein includes the decellularized heart described above and a population of regenerative cells attached thereto. In some embodiments, the regenerative cells are pluripotent cells. In some embodiment, the regenerative cells are embryonic stem cells, umbilical cord cells, adult-derived stem or progenitor cells, bone marrow-derived cells, blood-derived cells, mesenchymal stem cells (MSC), skeletal muscle-derived cells, multipotent adult progenitor cells (MAPC), cardiac stem cells (CSC), or multipotent adult cardiac-derived stem cells. In some embodiments, the regenerative cells are cardiac fibroblasts, cardiac microvasculature cells, or aortic endothelial cells.

Generally, the number of the regenerative cells attached to the decellularized heart is at least about 1,000. In some embodiments, the number of the regenerative cells attached to the decellularized heart is about 1,000 cells/mg tissue (wet weight; i.e., pre-decellularized weight) to about 10,000,000 cells/mg tissue (wet weight). In some embodiments, the regenerative cells are heterologous to the decellularized heart. Also in some embodiments, the solid organ is to be transplanted into a patient and the regenerative cells are autologous to the patient.

In yet another aspect, the invention provides a method of making a solid organ. Such a method generally includes providing a decellularized heart as described herein, and contacting the decellularized heart with a population of regenerative cells under conditions in which the regenerative cells engraft, multiply and/or differentiate within and on the decellularized heart. In one embodiment, the regenerative cells are injected or perfused into the decellularized heart.

In still another aspect, the invention provides for a method of decellularizing a heart. Such a method includes providing a heart, cannulating the heart at one or more than one cavity, vessel, and/or duct to produce a cannulated heart, and perfusing the cannulated heart with a first cellular disruption medium via the one or more than one cannulations. For example, the perfusion can be multi-directional from each cannulated cavity, vessel, and/or duct. Typically, the cellular disruption medium comprises at least one detergent such as SDS, PEG, or Triton X.

Such a method also can include perfusing the cannulated heart with a second cellular disruption medium via the more than one cannulations. Generally, the first cellular disruption medium can be an anionic detergent such as SDS and the second cellular disruption medium can be an ionic detergent such as Triton X. In such methods, the perfusing can be for about 2 to 12 hours per gram (wet weight) of heart tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Figure 1:
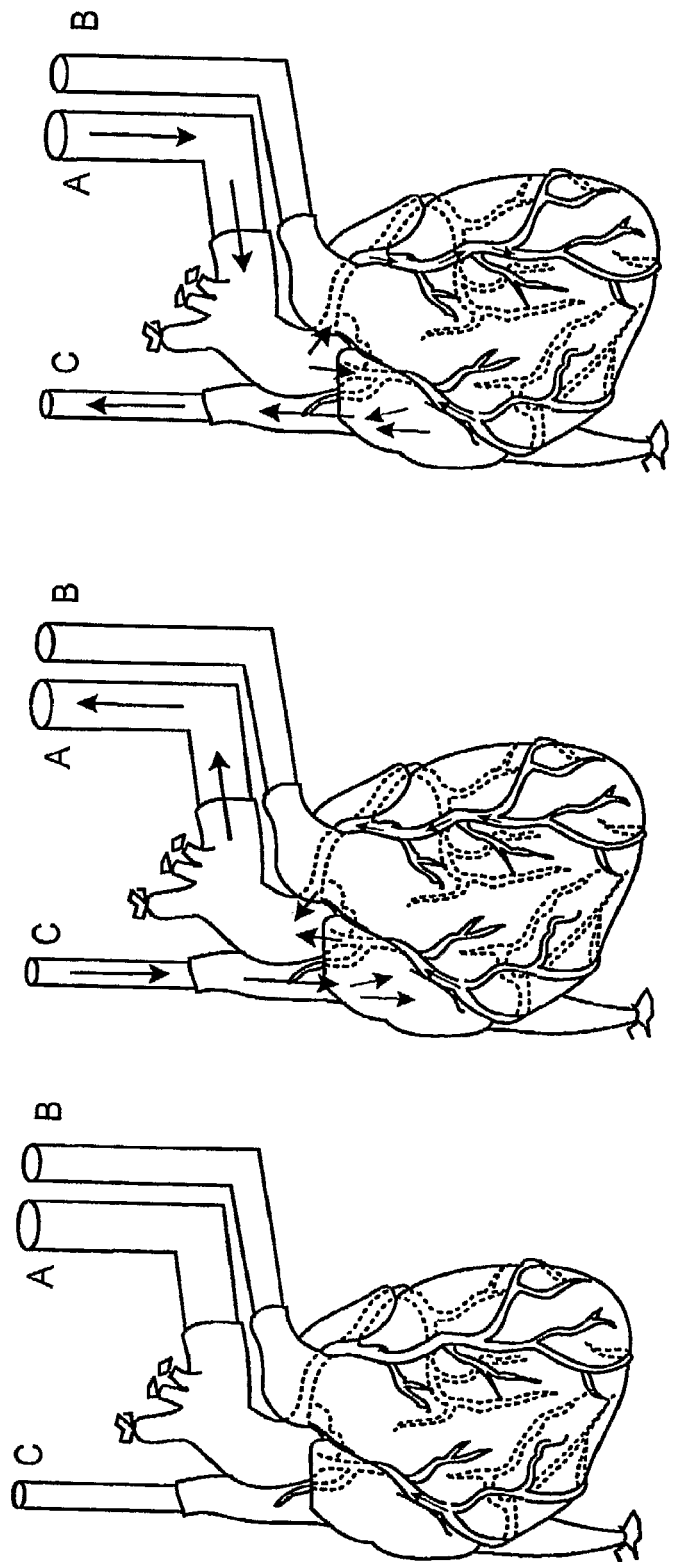
FIG. 1 is a schematic showing the initial preparation for the decellularization of a heart. The aorta, pulmonary artery, and superior caval vein are cannulated (A, B, C, respectively), and the inferior caval vein, brachiocephalic artery, left common carotid artery, and left subclavian artery are ligated. Arrows indicate the direction of perfusion in antegrade and retrograde.

Solid organs generally have three main components, the extracellular matrix (ECM), cells embedded therein, and a vasculature bed. Decellularization of a solid organ as described herein removes most or all of the cellular components while substantially preserving the extracellular matrix (ECM) and the vasculature bed. A decellularized solid organ then can be used as a scaffold for recellularization. Mammals from which solid organs can be obtained include, without limitation, rodents, pigs, rabbits, cattle, sheep, dogs, and humans. Organs and tissues used in the methods described herein can be cadaveric.

Solid organs as referred to herein include, without limitation, heart, liver, lungs, skeletal muscles, brain, pancreas, spleen, kidneys, uterus, and bladder. A solid organ as used herein refers to an organ that has a "substantially closed" vasculature system. A "substantially closed" vasculature system with respect to an organ means that, upon perfusion with a liquid, the majority of the liquid is contained within the solid organ and does not leak out of the solid organ, assuming the major vessels are cannulated, ligated, or otherwise restricted. Despite having a "substantially closed" vasculature system, many of the solid organs listed above have defined "entrance" and "exit" vessels which are useful for introducing and moving the liquid throughout the organ during perfusion.

In addition to the solid organs described above, other types of vascularized organs or tissues such as, for example, all or portions of joints (e.g., knees, shoulders, or hips), trachea, or spinal cord can be decellularized using the methods disclosed herein. Further, the methods disclosed herein also can be used to decellularize avascular tissues such as, for example, cartilage or cornea.

A decellularized organ or tissue as described herein (e.g., heart or liver) or any portion thereof (e.g., an aortic valve, a mitral valve, a pulmonary valve, a tricuspid valve, a pulmonary vein, a pulmonary artery, coronary vasculature, septum, a right atrium, a left atrium, a right ventricle, or a left ventricle), with or without recellularization, can be used for transplanting into a patient. Alternatively, a recellularized organ or tissue as described herein can be used to examine, for example, cells undergoing differentiation and/or the cellular organization of an organ or tissue.

Decellularization of Organs or Tissues

The invention provides for methods and materials to decellularize a mammalian organ or tissue. The initial step in decellularizing an organ or tissue is to cannulate the organ or tissue, if possible. The vessels, ducts, and/or cavities of an organ or tissue can be cannulated using methods and materials known in the art. The next step in decellularizing an organ or tissue is to perfuse the cannulated organ or tissue with a cellular disruption medium. Perfusion through an organ can be multi-directional (e.g., antegrade and retrograde). Langendorff perfusion of a heart is routine in the art, as is physiological perfusion (also known as four chamber working mode perfusion). See, for example, Dehnert, The Isolated Perfused Warm-Blooded Heart According to Langendorff, In Methods in Experimental Physiology and Pharmacology: Biological Measurement Techniques V. Biomesstechnik-Verlag March GmbH, West Germany, 1988. Briefly, for Langendorff perfusion, the aorta is cannulated and attached to a reservoir containing cellular disruption medium. A cellular disruption medium can be delivered in a retrograde direction down the aorta either at a constant flow rate delivered, for example, by an infusion or roller pump or by a constant hydrostatic pressure. In both instances, the aortic valves are forced shut and the perfusion fluid is directed into the coronary ostia (thereby perfusing the entire ventricular mass of the heart), which then drains into the right atrium via the coronary sinus. For working mode perfusion, a second cannula is connected to the left atrium and perfusion can be changed from retrograde to antegrade.

Methods are known in the art for perfusing other organ or tissues. By way of example, the following references describe the perfusion of lung, liver, kidney, brain, and limbs. Van Putte et al., 2002, *Ann. Thorac. Surg.*, 74(3):893-8; den Butter et al., 1995, *Transpl. Int.*, 8:466-71; Firth et al., 1989, *Clin. Sci.* (*Lond.*), 77(6):657-61; Mazzetti et al., 2004, *Brain Res.*, 999(1):81-90; Wagner et al., 2003, *J. Artif. Organs*, 6(3):183-91.

One or more cellular disruption media can be used to decellularize an organ or tissue. A cellular disruption medium generally includes at least one detergent such as SDS, PEG, or Triton X. A cellular disruption medium can include water such that the medium is osmotically incompatible with the cells. Alternatively, a cellular disruption medium can include a buffer (e.g., PBS) for osmotic compatibility with the cells. Cellular disruption media also can include enzymes such as, without limitation, one or more collagenases, one or more dispases, one or more DNases, or a protease such as trypsin. In some instances, cellular disruption media also or alternatively can include inhibitors of one or more enzymes (e.g., protease inhibitors, nuclease inhibitors, and/or collegenase inhibitors).

In certain embodiments, a cannulated organ or tissue can be perfused sequentially with two different cellular disruption media. For example, the first cellular disruption medium can include an anionic detergent such as SDS and the second cellular disruption medium can include an ionic detergent such as Triton X. Following perfusion with at least one cellular disruption medium, a cannulated organ or tissue can be perfused, for example, with wash solutions and/or solutions containing one or more enzymes such as those disclosed herein. Alternating the direction of perfusion (e.g., antegrade and retrograde) can help to effectively decellularize the entire organ or tissue. Decellularization as described herein essentially decellularizes the organ from the inside out, resulting in very little damage to the ECM. An organ or tissue can be decellularized at a suitable temperature between 4 and 40° C. Depending upon the size and weight of an organ or tissue and the particular detergent(s) and concentration of detergent(s) in the cellular disruption medium, an organ or tissue generally is perfused from about 2 to about 12 hours per gram of solid organ or tissue with cellular disruption medium. Including washes, an organ may be perfused for up to about 12 to about 72 hours per gram of tissue. Perfusion generally is adjusted to physiologic conditions including pulsatile flow, rate and pressure.

As indicated herein, a decellularized organ or tissue consists essentially of the extracellular matrix (ECM) component of all or most regions of the organ or tissue, including ECM components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Successful decellularization is defined as the absence of detectable myofilaments, endothelial cells, smooth muscle cells, and nuclei in histologic sections using standard histological staining procedures. Preferably, but not necessarily, residual cell debris also has been removed from the decellularized organ or tissue.

To effectively recellularize and generate an organ or tissue, it is important that the morphology and the architecture of the ECM be maintained (i.e., remain substantially intact) during and following the process of decellularization. "Morphology" as used herein refers to the overall shape of the organ or tissue or of the ECM, while "architecture" as used herein refers to the exterior surface, the interior surface, and the ECM therebetween.

The morphology and architecture of the ECM can be examined visually and/or histologically. For example, the basal lamina on the exterior surface of a solid organ or within the vasculature of an organ or tissue should not be removed or significantly damaged due to decellularization. In addition, the fibrils of the ECM should be similar to or significantly unchanged from that of an organ or tissue that has not been decellularized.

One or more compounds can be applied in or on a decellularized organ or tissue to, for example, preserve the decellularized organ, or to prepare the decellularized organ or tissue for recellularization and/or to assist or stimulate cells during the recellularization process. Such compounds include, but are not limited to, one or more growth factors (e.g., VEGF, DKK-1, FGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized organ or tissue can be further treated with, for example, irradiation (e.g., UV, gamma) to reduce or eliminate the presence of any type of microorganism remaining on or in a decellularized organ or tissue.

Recellularization of Organs or Tissues

The invention provides for materials and methods for generating an organ or tissue. An organ or tissue can be generated by contacting a decellularized organ or tissue as described herein with a population of regenerative cells. Regenerative cells as used herein are any cells used to recellularize a decellularized organ or tissue. Regenerative cells can be totipotent cells, pluripotent cells, or multipotent cells, and can be uncommitted or committed. Regenerative cells also can be single-lineage cells. In addition, regenerative cells can be undifferentiated cells, partially differentiated cells, or fully differentiated cells. Regenerative cells as used herein include embryonic stem cells (as defined by the National Institute of Health (NIH); see, for example, the Glossary at stemcells.nih.gov on the World Wide Web). Regenerative cells also include progenitor cells, precursor cells, and "adult"-derived stem cells including umbilical cord cells and fetal stem cells.

Examples of regenerative cells that can be used to recellularize an organ or tissue include, without limitation, embryonic stem cells, umbilical cord blood cells, tissue-derived stem or progenitor cells, bone marrow-derived step or progenitor cells, blood-derived stem or progenitor cells, mesenchymal stem cells (MSC), skeletal muscle-derived cells, or multipotent adult progenitor cells (MAPC). Additional regenerative cells that can be used include cardiac stem cells (CSC), multipotent adult cardiac-derived stem cells, cardiac fibroblasts, cardiac microvasculature endothelial cells, or aortic endothelial cells. Bone marrow-derived stem cells such as bone marrow mononuclear cells (BM-MNC), endothelial or vascular stem or progenitor cells, and peripheral blood-derived stem cells such as endothelial progenitor cells (EPC) also can be used as regenerative cells.

The number of regenerative cells that is introduced into and onto a decellularized organ in order to generate an organ or tissue is dependent on both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be "seeded" with at least about 1,000 (e.g., at least 10,000, 100,000, 1,000,000, 10,000,000, or 100,000,000) regenerative cells; or can have from about 1,000 cells/mg tissue (wet weight, i.e., prior to decellularization) to about 10,000,000 cells/mg tissue (wet weight) attached thereto.

Regenerative cells can be introduced ("seeded") into a decellularized organ or tissue by injection into one or more locations. In addition, more than one type of cell (i.e., a cocktail of cells) can be introduced into a decellularized organ or tissue. For example, a cocktail of cells can be injected at multiple positions in a decellularized organ or tissue or different cell types can be injected into different portions of a decellularized organ or tissue. Alternatively, or in addition to injection, regenerative cells or a cocktail of cells can be introduced by perfusion into a cannulated decellularized organ or tissue. For example, regenerative cells can be perfused into a decellularized organ using a perfusion medium, which can then be changed to an expansion and/or differentiation medium to induce growth and/or differentiation of the regenerative cells.

During recellularization, an organ or tissue is maintained under conditions in which at least some of the regenerative cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or tissue and the regenerative cells attached thereto are maintained in a suitable environment. For example, the regenerative cells may require a nutritional supplement (e.g., nutrients and/or a carbon source such as glucose), exogenous hormones or growth factors, and/or a particular pH.

Regenerative cells can be allogeneic to a decellularized organ or tissue (e.g., a human decellularized organ or tissue seeded with human regenerative cells), or regenerative cells can be xenogeneic to a decellularized organ or tissue (e.g., a pig decellularized organ or tissue seeded with human regenerative cells). "Allogeneic" as used herein refers to cells obtained from the same species as that from which the organ or tissue originated (e.g., related or unrelated individuals), while "xenogeneic" as used herein refers to cells obtained from a species different than that from which the organ or tissue originated.

In some instances, an organ or tissue generated by the methods described herein is to be transplanted into a patient. In those cases, the regenerative cells used to recellularize a decellularized organ or tissue can be obtained from the patient such that the regenerative cells are "autologous" to the patient. Regenerative cells from a patient can be obtained from, for example, blood, bone marrow, tissues, or organs at different stages of life (e.g., prenatally, neonatally or perinatally, during adolescence, or as an adult) using methods known in the art. Alternatively, regenerative cells used to recellularize a decellularized organ or tissue can be syngeneic (i.e., from an identical twin) to the patient, regenerative cells can be human lymphocyte antigen (HLA)-matched cells from, for example, a relative of the patient or an HLA-matched individual unrelated to the patient, or regenerative cells can be allogeneic to the patient from, for example, a non-HLA-matched donor.

Irrespective of the source of the regenerative cells (e.g., autologous or not), the decellularized solid organ can be autologous, allogeneic or xenogeneic to a patient.

In certain instances, a decellularized organ may be recellularized with cells in vivo (e.g., after the organ or tissue has been transplanted into an individual). In vivo recellularization may be performed as described above (e.g., injection and/or perfusion) with, for example, any of the regenerative cells described herein. Alternatively or additionally, in vivo seeding of a decellularized organ or tissue with endogenous cells may occur naturally or be mediated by factors delivered to the recellularized tissue.

The progress of regenerative cells can be monitored during recellularization. For example, the number of cells on or in an organ or tissue can be evaluated by taking a biopsy at one or more time points during recellularization. In addition, the amount of differentiation that regenerative cells have undergone can be monitored by determining whether or not various markers are present in a cell or a population of cells. Markers associated with different cells types and different stages of differentiation for those cell types are known in the art, and can be readily detected using antibodies and standard immunoassays. See, for example, *Current Protocols in Immunology*, 2005, Coligan et al., Eds., John Wiley & Sons, Chapters 3 and 11. Nucleic acid assays as well as morphological and/or histological evaluation can be used to monitor recellularization.

Controlled System for Decellularizing and/or Recellularizing an Organ or Tissue

The invention also provides for a system (e.g., a bioreactor) for decellularizing and/or recellularizing an organ or tissue. Such a system generally includes at least one cannulation device for cannulating an organ or tissue, a perfusion apparatus for perfusing the organ or tissue through the cannula(s), and means (e.g., a containment system) to maintain a sterile environment for the organ or tissue. Cannulation and perfusion are well-known techniques in the art. A cannulation device generally includes size-appropriate hollow tubing for introducing into a vessel, duct, and/or cavity of an organ or tissue. Typically, one or more vessels, ducts, and/or cavities are cannulated in an organ. A perfusion apparatus can include a holding container for the liquid (e.g., a cellular disruption medium) and a mechanism for moving the liquid through the organ (e.g., a pump, air pressure, gravity) via the one or more cannulae. The sterility of an organ or tissue during decellularization and/or recellularization can be maintained using a variety of techniques known in the art such as controlling and filtering the air flow and/or perfusing with, for example, antibiotics, anti-fungals or other anti-microbials to prevent the growth of unwanted microorganisms.

A system to decellularize and recellularize organ or tissues as described herein can possess the ability to monitor certain perfusion characteristics (e.g., pressure, volume, flow pattern, temperature, gases, pH), mechanical forces (e.g., ventricular wall motion and stress), and electrical stimulation (e.g., pacing). As the coronary vascular bed changes over the course of decellularization and recellularization (e.g. vascular resistance, volume), a pressure-regulated perfusion apparatus is advantageous to avoid large fluctuations. The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the system (e.g., bioreactor) and/or the organ or tissue. Sonomicromentry, micromanometry, and/or conductance measurements can be used to acquire pressure-volume or preload recruitable stroke work information relative to myocardial wall motion and performance. For example, sensors can be used to monitor the pressure of a liquid moving through a cannulated organ or tissue; the ambient temperature in the system and/or the temperature of the organ or tissue; the pH and/or the rate of flow of a liquid moving through the cannulated organ or tissue; and/or the biological activity of a recellularizing organ or tissue. In addition to having sensors for monitoring such features, a system for decellularizing and/or recellularizing an organ or tissue also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, an external pacemaker, and/or a compliance chamber. To help ensure stable conditions (e.g., temperature), the chambers, reservoirs and tubings can be water-jacketed.

It can be advantageous during recellularization to place a mechanical load on the organ and the cells attached thereto. As an example, a balloon inserted into the left ventricle via the left atrium can be used to place mechanical stress on a heart. A piston pump that allows adjustment of volume and rate can be connected to the balloon to simulate left ventricular wall motion and stress. To monitor wall motion and stress, left ventricular wall motion and pressure can be measured using micromanometry and/or sonomicrometry. In some embodiments, an external pacemaker can be connected to a piston pump to provide synchronized stimulation with each deflation of the ventricular balloon (which is equivalent to the systole). Peripheral ECG can be recorded from the heart surface to allow for the adjustment of pacing voltage, the monitoring of de- and repolarization, and to provide a simplified surface map of the recellularizing or recellularized heart.

Mechanical ventricular distention can also be achieved by attaching a peristaltic pump to a canula inserted into the left ventricle through the left atrium. Similar to the procedure described above involving a balloon, ventricular distention achieved by periodic fluid movement (e.g., pulsatile flow) through the canula can be synchronized with electrical stimulation.

Using the methods and materials disclosed herein, a mammalian heart can be decellularized and recellularized and, when maintained under the appropriate conditions, a functional heart that undergoes contractile function and responds to pacing stimuli and/or pharmacologic agents can be generated. This recellularized functional heart can be transplanted into a mammal and function for a period of time.

Figure 2:
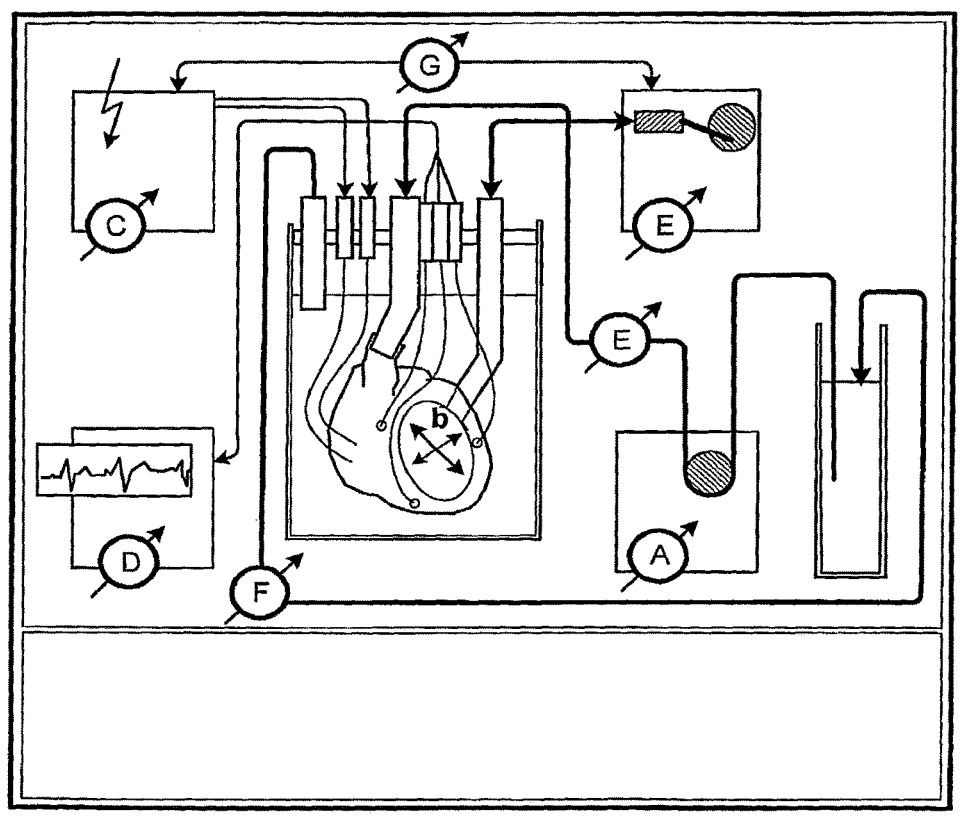
FIG. 2 is a schematic of one embodiment of a decellularization/recellularization apparatus.

FIG. 2 shows one embodiment of a system for decellularizing and/or recellularizing an organ or tissue (e.g., a bioreactor). The embodiment shown is a bioreactor for decellularizing and recellularizing a heart. This embodiment has an adjustable rate and volume peristaltic pump (A); an adjustable rate and volume piston pump connected to an intraventricular balloon (B); an adjustable voltage, frequency and amplitude external pacemaker (C); an ECG recorder (D); a pressure sensor in the 'arterial line' (which equals coronary artery pressure) (E); a pressure sensor in the 'venous' line (which equals coronary sinus pressure) (F); and synchronization between the pacemaker and the piston pump (G).

A system for generating an organ or tissue can be controlled by a computer-readable storage medium in combination with a programmable processor (e.g., a computer-readable storage medium as used herein has instructions stored thereon for causing a programmable processor to perform particular steps). For example, such a storage medium, in combination with a programmable processor, can receive and process information from one or more of the sensors. Such a storage medium in conjunction with a programmable processor also can transmit information and instructions back to the bioreactor and/or the organ or tissue.

An organ or tissue undergoing recellularization can be monitored for biological activity. The biological activity can be that of the organ or tissue itself such as electrical activity, mechanical activity, mechanical pressure, contractility, and/or wall stress of the organ or tissue. In addition, the biological activity of the cells attached to the organ or tissue can be monitored, for example, for ion transport/exchange activity, cell division, and/or cell viability. See, for example, Laboratory Textbook of Anatomy and Physiology (2001, Wood, Prentice Hall) and Current Protocols in Cell Biology (2001, Bonifacino et al., Eds, John Wiley & Sons). As discussed above, it may be useful to simulate an active load on an organ during recellularization. A computer-readable storage medium of the invention, in combination with a programmable processor, can be used to coordinate the components necessary to monitor and maintain an active load on an organ or tissue.

In one embodiment, the weight of an organ or tissue can be entered into a computer-readable storage medium as described herein, which, in combination with a programmable processor, can calculate exposure times and perfusion pressures for that particular organ or tissue. Such a storage medium can record preload and afterload (the pressure before and after perfusion, respectively) and the rate of flow. In this embodiment, for example, a computer-readable storage medium in combination with a programmable processor can adjust the perfusion pressure, the direction of perfusion, and/or the type of perfusion solution via one or more pumps and/or valve controls.

In accordance with the present invention, there may be employed conventional molecular biology, microbiology, biochemical, and cell biology techniques within the skill of the art. Such techniques are explained fully in the literature. The invention will be further described in the following examples, which do not limit the scope of the invention described in the claims.

EXAMPLES

Section A. Decellularization (Part I)

Example 1—Preparation of a Solid Organ for Decellularization

To avoid the formation of post mortal thrombi, a donor rat was systemically heparinized with 400 U of heparin/kg of donor. Following heparinization, the heart and the adjacent large vessels were carefully removed.

The heart was placed in a physiologic saline solution (0.9%) containing heparin (2000 U/ml) and held at 5° C. until further processing. Under sterile conditions, the connective tissue was removed from the heart and the large vessels. The inferior venae cava and the left and right pulmonary veins were ligated distal from the right and left atrium using monofil, non-resorbable ligatures.

Example 2—Cannulation and Perfusion of a Solid Organ

The heart was mounted on a decellularization apparatus for perfusion (FIG. 1). The descending thoracic artery was cannulated to allow retrograde coronary perfusion (FIG. 1, Cannula A). The branches of the thoracic artery (e.g., brachiocephalic trunc, left common carotid artery, left subclavian artery) were ligated. The pulmonary artery was cannulated before its division into the left and right pulmonary artery (FIG. 1, Cannula B). The superior vena cava was cannulated (FIG. 1, Cannula C). This configuration allows for both retrograde and antegrade coronary perfusion.

When positive pressure was applied to the aortic cannula (A), perfusion occurred from the coronary arteries through the capillary bed to the coronary venous system to the right atrium and the superior caval vein (C). When positive pressure was applied to the superior caval vein cannula (C), perfusion occurred from the right atrium, the coronary sinus, and the coronary veins through the capillary bed to the coronary arteries and the aortic cannula (A).

Example 3—Decellularization

After the heart was mounted on the decellularization apparatus, antegrade perfusion was started with cold, heparinized, calcium-free phosphate buffered solution containing 1-5 mmol adenosine per L perfusate to reestablish constant coronary flow. Coronary flow was assessed by measuring the coronary perfusion pressure and the flow, and calculating coronary resistance. After 15 minutes of stable coronary flow, the detergent-based decellularization process was initiated.

The details of the procedures are described below. Briefly, however, a heart was perfused antegradely with a detergent. After perfusion, the heart can be flushed with a buffer (e.g., PBS) retrogradely. The heart then was perfused with PBS containing antibiotics and then PBS containing DNase I. The heart then was perfused with 1% benzalkonium chloride to reduce microbial contamination and to prevent future microbial contamination, and then perfused with PBS to wash the organ of any residual cellular components, enzymes, or detergent.

Example 4—Decellularization of Cadaveric Rat Hearts

Hearts were isolated from 8 male nude rats (250-300 g). Immediately after dissection, the aortic arch was cannulated and the hearts were retrogradely perfused with the indicated detergent. The four different detergent-based decellularization protocols (see below) were compared with respect to their feasibility and efficacy in (a) removing cellular components and (b) preserving vascular structures.

Decellularization generally included the following steps: stabilization of the solid organ, decellularization of the solid organ, renaturation and/or neutralization of the solid organ, washing the solid organ, degradation of any DNA remaining on the organ, disinfection of the organ, and homeostasis of the organ.

A) Decellularization Protocol #1 (PEG)

Hearts were washed in 200 ml PBS containing 100 U/ml penicillin, 0.1 mg/ml Streptomycin, and 0.25 µg/ml Amphotericin B with no recirculation. Hearts were then decellularized with 35 ml polyethyleneglycol (PEG; 1 g/ml) for up to 30 minutes with manual recirculation. The organ was then washed with 500 ml PBS for up to 24 hours using a pump for recirculation. The washing step was repeated at least twice for at least 24 hours each time. Hearts were exposed to 35 ml DNase I (70 U/ml) for at least 1 hour with manual recirculation. The organs were washed again with 500 ml PBS for at least 24 hours.

B) Decellularisation Protocol #2 (Triton X and Trypsin)

Hearts were washed in 200 ml PBS containing 100 U/ml Penicillin, 0.1 mg/ml Streptomycin, and 0.25 µg/ml Amphotericin B for at least about 20 minutes with no recirculation. Hearts were then decellularized with 0.05% Trypsin for 30 min followed by perfusion with 500 ml PBS containing 5% Triton-X and 0.1% ammonium-hydroxide for about 6 hours. Hearts were perfused with deionized water for about 1 hour, and then perfused with PBS for 12 h. Hearts were then washed 3 times for 24 hours each time in 500 ml PBS using a pump for recirculation. The hearts were perfused with 35 ml DNase I (70 U/ml) for 1 hour with manual recirculation and washed twice in 500 ml PBS for at least about 24 hours each time using a pump for recirculation.

C) Decellularization Protocol #3 (1% SDS)

Hearts were washed in 200 ml PBS containing 100 U/ml Penicillin, 0.1 mg/ml Streptomycin, and 0.25 µg/ml Amphotericin B for at least about 20 mins with no recirculation. The hearts were decellularized with 500 ml water containing 1% SDS for at least about 6 hours using a pump for recirculation. The hearts were then washed with deionized water for about 1 hour and washed with PBS for about 12 hours. The hearts were washed three times with 500 ml PBS for at least about 24 hours each time using a pump for recirculation. The heart was then perfused with 35 ml DNase I (70 U/ml) for about 1 hour using manual recirculation, and washed three times with 500 ml PBS for at least about 24 hours each time using a pump for recirculation.

D) Decellularisation Protocol #4 (Triton X)

Hearts were washed with 200 ml PBS containing 100 U/ml Penicillin, 0.1 mg/ml Streptomycin, and 0.25 µg/ml Amphotericin B for at least about 20 mins with no recirculation. Hearts were then decellularized with 500 ml water containing 5% Triton X and 0.1% ammonium hydroxide for at least 6 hours using a pump for recirculation. Hearts were then perfused with deionized water for about 1 hour and then with PBS for about 12 hours. Hearts were washed by perfusing with 500 ml PBS 3 times for at least 24 hours each time using a pump for recirculation. Hearts were then perfused with 35 ml DNase I (70 U/ml) for about 1 hour using manual recirculation, and washed three times in 500 ml PBS for about 24 hours each time.

For initial experiments, the decellularisation apparatus was set up within a laminar flow hood. Hearts were perfused at a coronary perfusion pressure of 60 cm $H_2O$. Although not required, the hearts described in the experiments above were mounted in a decellularisation chamber and completely submerged and perfused with PBS containing antibiotics for 72 hours in recirculation mode at a continuous flow of 5 ml/min to wash out as many cellular components and detergent as possible.

Successful decellularization was defined as the lack of myofilaments and nuclei in histologic sections. Successful preservation of vascular structures was assessed by perfusion with 2% Evans Blue prior to embedding tissue sections.

Highly efficient decellularization took place when a heart was first perfused antegradely with an ionic detergent (1% sodium-dodecyl-sulfate (SDS), approximately 0.03 M) dissolved in deionized $H_2O$ at a constant coronary perfusion pressure and then was perfused antegradely with a non-ionic detergent (1% Triton X-100) to remove the SDS and presumably to renature the extracellular matrix (ECM) proteins. Intermittently, the heart was perfused retrogradely with phosphate buffered solution to clear obstructed capillaries and small vessels.

Example 5—Evaluation of Decellularized Organs

To demonstrate intact vascular structures following decellularization, a decellularized heart is stained via Langendorff perfusion with Evans Blue to stain vascular basement membrane and quantify macro- and micro-vascular density. Further, polystyrene particles can be perfused into and through a heart to quantify coronary volume, the level of vessel leakage, and to assess the distribution of perfusion by analyzing coronary effluent and tissue sections. A combination of three criteria are assessed and compared to isolated non-decellularised heart: 1) an even distribution of polystyrene particles, 2) significant change in leakiness at some level 3) microvascular density.

Fiber orientation is assessed by the polarized-light microscopy technique of Tower et al. (2002, Fiber alignment imaging during mechanical testing of soft tissues, *Ann Biomed Eng.*, 30(10):1221-33), which can be applied in real-time to a sample subjected to uniaxial or biaxial stress. During Langendorff perfusion, basic mechanical properties of the decellularised ECM are recorded (compliance, elasticity, burst pressure) and compared to freshly isolated hearts.

Section B. Decellularization (Part II)

Example 1—Decellularization of Rat Heart

Male 12 week old F344 Fischer rats (Harlan Labs, PO Box 29176 Indianapolis, Ind. 46229), were anesthetized using intraperitoneal injection of 100 mg/kg ketamine (Phoenix Pharmaceutical, Inc., St. Joseph, Mo.) and 10 mg/kg xylazine (Phoenix Pharmaceutical, Inc., St. Joseph, Mo.). After systemic heparinization (American Pharmaceutical Partners, Inc., Schaumberg, Ill.) through the left femoral vein, a median sternotomy was performed and the pericardium was opened. The retrosternal fat body was removed, the ascending thoracic aorta was dissected and its branches ligated. The caval and pulmonary veins, the pulmonary artery and the thoracic aorta were transsected and the heart was removed from the chest. A prefilled 1.8 mm aortic canula (Radnoti Glass, Monrovia, Calif.) was inserted into the ascending aorta to allow retrograde coronary perfusion (Langendorff). The hearts were perfused with heparinized PBS (Hyclone, Logan, Utah) containing 10 µM adenosine at a coronary perfusion pressure of 75 cm $H_2O$ for 15 minutes followed by 1% sodium dodecyl sulfate (SDS) or 1% polyethylene glycol 1000 (PEG 1000) (EMD Biosciences, La Jolla, Germany) or 1% Triton-X 100 (Sigma, St. Louis, Mo.) in deionized water for 2-15 hours. This was followed by 15 minutes of deionized water perfusion and 30 minutes of perfusion with 1% Triton-X (Sigma, St. Louis, Mo.) in deionized water. The hearts were then continuously perfused with antibiotic-containing PBS (100 U/ml penicillin-G (Gibco, Carlsbad, Calif.), 100 U/ml streptomycin (Gibco, Carlsbad, Calif.) and 0.25 µg/ml Amphotericin B (Sigma, St. Louis, Mo.)) for 124 hours.

After 420 minutes of retrograde perfusion with either 1% PEG, 1% Triton-X 100 or 1% SDS, PEG and Triton-X 100 perfusion induced an edematous, opaque appearance, while SDS perfusion resulted in a more dramatic change leading to a nearly translucent graft as opaque elements were slowly washed out. Hearts exposed to all three protocols remained grossly intact with no evidence of coronary rupture or aortic valve insufficiency throughout the perfusion protocol (at constant coronary perfusion pressure of 77.4 mmHg). Coronary flow decreased in all three protocols during the first 60 minutes of perfusion, then normalized during SDS perfusion while remaining increased in Triton-X 100 and PEG perfusion. SDS perfusion induced the highest initial increase in calculated coronary resistance (up to 250 mmHg·s·ml$^{-1}$), followed by Triton-X (up to 200 mmHg·s·ml$^{-1}$) and PEG (up to 150 mmHg·s·ml$^{-1}$).

Using histological sections of the detergent perfused heart tissue, it was determined that decellularization over the observed time period was incomplete in both PEG and Triton-X 100 treated hearts; Hematoxylin-Eosin (H&E) staining showed nuclei and cross-striated filaments. In contrast, no nuclei or contractile filaments were detectable in sections of SDS-perfused hearts. Vascular structures and ECM fiber direction, however, were preserved in the SDS-treated hearts.

To remove the ionic SDS from the ECM after the initial decellularization, the organ was perfused for 30 minutes with Triton-X 100. In addition and to ensure complete washout of all detergents and to reestablish a physiologic pH, the decellularized organ was perfused extensively with deionized water and PBS for 124 h.

Example 2—Decellularization of Rat Kidney

For kidney isolation, the entire peritoneal content was wrapped in wet gauze and carefully mobilized to the side to expose the retroperitoneal space. The mesenteric vessels were ligated and transected. The abdominal aorta was ligated and transected below the take off of the renal arteries. The thoracic aorta was transected just above the diaphragm and canulated using a 1.8 mm aortic canula (Radnoti Glass, Monrovia, Calif.). The kidneys were carefully removed from the retroperitoneum and submerged in sterile PBS (Hyclone, Logan, Utah) to minimize pulling force on the renal arteries. 15 minutes of heparinized PBS perfusion were followed by 2-16 hours of perfusion with 1% SDS (Invitrogen, Carlsbad, Calif.) in deionized water and 30 minutes of perfusion with 1% Triton-X (Sigma, St. Louis, Mo.) in deionized water. The liver was then continuously perfused with antibiotic containing PBS (100 U/ml penicillin-G (Gibco, Carlsbad, Calif.), 100 U/ml streptomycin (Gibco, Carlsbad, Calif.), 0.25 µg/ml Amphotericin B (Sigma, St. Louis, Mo.)) for 124 hours.

420 minutes of SDS perfusion followed by Triton-X 100 yielded a completely decellularized renal ECM scaffold with intact vasculature and organ architecture. Evans blue perfusion confirmed intact vasculature similar to decellularized cardiac ECM. Movat pentachrome staining of decellularized renal cortex showed intact glomeruli and proximal and distal convoluted tubule basement membranes without any intact cells or nuclei. Staining of decellularized renal medulla showed intact tubule and collecting duct basement membranes. SEM of decellularized renal cortex confirmed intact glomerular and tubular basement membranes. Characteristic structures such as Bowman's capsule delineating the glomerulus from surrounding proximal and distal tubules and glomerular capillary basement membranes within the glomeruli were preserved. SEM images of decellularized renal medulla showed intact medullary pyramids reaching into the renal pelvis with intact collecting duct basal membranes leading towards the papilla. Thus, all the major ultrastructures of the kidney were intact after decellularization.

Example 3—Decellularization of Rat Lung

The lung (with the trachea) were carefully removed from the chest and submerged in sterile PBS (Hyclone, Logan, Utah) to minimize pulling force on the pulmonary arteries. 15 minutes of heparinized PBS perfusion was followed by 2-12 hours of perfusion with 1% SDS (Invitrogen, Carlsbad, Calif.) in deionized water and 15 minutes of perfusion with 1% Triton-X (Sigma, St. Louis, Mo.) in deionized water. The lung was then continuously perfused with antibiotic containing PBS (100 U/ml penicillin-G (Gibco, Carlsbad, Calif.), 100 U/ml streptomycin (Gibco, Carlsbad, Calif.), 0.25 µg/ml Amphotericin B (Sigma, St. Louis, Mo.)) for 124 hours.

180 minutes of SDS perfusion followed by Triton-X 100 perfusion yielded a completely decellularized pulmonary ECM scaffold with intact airways and vessels. Movat pentachrome staining of histologic sections showed the presence of ECM components in lung including major structural proteins such as collagen and elastin and also soluble elements such as proteoglycans. However, no nuclei or intact cells were retained. Airways were preserved from the main bronchus to terminal bronchiole to respiratory bronchioles, alveolar ducts and alveoles. The vascular bed from pulmonary arteries down to the capillary level and pulmonary veins remained intact. SEM micrographs of decellularized lung showed preserved bronchial, alveolar and vascular basement membranes with no evidence of retained cells. The meshwork of elastic and reticular fibers providing the major structural support to the interalveolar septum as well as the septal basement membrane were intact, including the dense network of capillaries within the pulmonary interstitium.

SEM micrographs of the decellularized trachea showed intact ECM architecture with decellularized hyaline cartilage rings and a rough luminal basal membrane without respiratory epithelium.

Example 4—Decellularization of Rat Liver

For liver isolation, the caval vein was exposed through a median laparotomy, dissected and canulated using a mouse aortic canula (Radnoti Glass, Monrovia, Calif.). The hepatic artery and vein and the bile duct were transsected and the liver was carefully removed from the abdomen and submerged in sterile PBS (Hyclone, Logan, Utah) to minimize pulling force on portal vein. 15 minutes of heparinized PBS perfusion was followed by 2-12 hours of perfusion with 1% SDS (Invitrogen, Carlsbad, Calif.) in deionized water and 15 minutes of 1% Triton-X (Sigma, St. Louis, Mo.) in deionized water. The liver was then continuously perfused with antibiotic containing PBS (100 U/ml penicillin-G (Gibco, Carlsbad, Calif.), 100 U/ml streptomycin (Gibco, Carlsbad, Calif.), 0.25 µg/ml Amphotericin B (Sigma, St. Louis, Mo.)) for 124 hours.

120 minutes of SDS perfusion followed by perfusion with Triton-X 100 were sufficient to generate a completely decellularized liver. Movat pentachrome staining of decellularized liver confirmed retention of characteristic hepatic organization with central vein and portal space containing hepatic artery, bile duct and portal vein.

Example 5—Methods and Materials Used to Evaluate the Decellularized Organs

Histology and Immunofluorescence. Movat Pentachrome staining was performed on paraffin embedded decellularized tissues following the manufacturers instructions (American Mastertech Scientific, Lodi, Calif.). Briefly, deparaffinized slides were stained using Verhoeff's elastic stain, rinsed, differentiated in 2% ferric chloride, rinsed, placed in 5% sodium thiosulfate, rinsed, blocked in 3% glacial acetic acid, stained in 1% alcian blue solution, rinsed, stained in crocein scarlet—acid fuchsin, rinsed, dipped in 1% glacial acetic acid, destained in 5% phosphotungstic acid, dipped in 1% glacial acetic acid, dehydrated, placed in alcoholic saffron solution, dehydrated, mounted and covered.

Immunofluorescence staining was performed on decellularized tissues. Antigen retrieval was performed on paraffin-embedded tissue (recellularized tissue) but not on frozen sections (decellularized tissue) as follows: Paraffin sections were de-waxed and rehydrated by 2 changes of xylene for 5 minutes each, followed by sequential alcohol gradient and rinsing in cold running tap water. The slides were then placed in antigen retrieval solution (2.94 g tri-sodium citrate, 22 ml of 0.2 M hydrochloric acid solution, 978 ml ultra-pure water, and adjusted to a pH of 6.0) and boiled for 30 minutes. After rinsing under running cold tap water for 10 minutes, immunostaining was begun. Frozen sections were fixed with 4% paraformaldehyde (Electron Microscopy Sciences, Hatfield, Pa.) in 1×PBS (Mediatech, Herndon, Va.) for 15 minutes at room temperature before staining. Slides were blocked with 4% Fetal Bovine Serum (FBS; HyClone, Logan, Utah) in 1×PBS for 30 minutes at room temperature. Samples were sequentially incubated for one hour at room temperature with diluted primary and secondary antibodies (Ab). Between each step, slides were washed 3 times (5-10 min each) with 1×PBS. Primary Ab against Collagen I (goat polyclonal IgG (Cat. No. sc-8788), Santa Cruz Biotechnology Inc., Santa Cruz, Calif.), Collagen III (goat polyclonal IgG (Cat. No. sc-2405), Santa Cruz Biotechnology Inc., Santa Cruz, Calif.), Fibronectin (goat polyclonal IgG (Cat. No. sc-6953), Santa Cruz Biotechnology Inc., Santa Cruz, Calif.), and Laminin (rabbit polyclonal IgG (Cat. No. sc-20142), Santa Cruz Biotechnology Inc., Santa Cruz, Calif.) were used at a 1:40 dilution with blocking buffer. Secondary Ab's bovine anti-goat IgG phycoerythin (Cat. No. sc-3747, Santa Cruz Biotechnology Inc., Santa Cruz, Calif.) and bovine anti-rabbit IgG phycoerythin (Cat. No. sc-3750, Santa Cruz Biotechnology Inc., Santa Cruz, Calif.) were used at a 1:80 dilution with blocking buffer. Slides were covered with cover glass (Fisherbrand 22×60, Pittsburgh, Pa.) in hardening mounting medium containing 4',6-diamidino-2-phenylindole (DAPI) (Vectashield, Vector Laboratories, Inc., Burlingame, Calif.). Images were recorded using ImagePro Plus 4.5.1 (Mediacybernetics, Silver Spring, Md.) on a Nikon Eclipse TE200 inverted microscope (Fryer Co. Inc., Huntley, Ill.) using ImagePro Plus 4.5.1 (Mediacybernetics, Silver Spring, Md.).

Scanning Electron Microscopy. Normal and decellularized tissues were perfusion fixed with 2.5% glutaraldehyde (Electron Microscopy Sciences, Hatfield, Pa.) in 0.1 M cacodylate buffer (Electron Microscopy Sciences, Hatfield, Pa.) for 15 minutes. Tissues were then rinsed two times in 0.1 M cacodylate buffer for 15 minutes. Post-fixation was performed with 1% osmium tetroxide (Electron Microscopy Sciences, Hatfield, Pa.) for 60 minutes. Tissue samples were then dehydrated in increasing concentrations of EtOH (50% for 10 minutes, 70% for 10 minutes two times, 80% for 10 minutes, 95% for 10 minutes two times, 100% for 10 minutes two times). Tissue samples then underwent critical point drying in a Tousimis Samdri-780A (Tousimis, Rockville, Md.). Coating was performed with 30 seconds of Gold/Palladium sputter coating in the Denton DV-502A Vacuum Evaporator (Denton Vacuum, Moorestown, N.J.). Scanning electron microscopy images were taken using a Hitachi 54700 Field Emission Scanning Electron Microscope (Hitachi High Technologies America, Pleasanton, Calif.).

Mechanical Testing. Crosses of myocardial tissue were cut from the left ventricle of rats so that the center area was approximately 5 mm×5 mm and the axes of the cross were aligned in the circumferential and longitudinal directions of the heart. The initial thickness of the tissue crosses were measured by a micrometer and found to be 3.59±0.14 mm in the center of the tissue cross. Crosses were also cut from decellularized rat left ventricular tissue in the same orientation and with the same center area size. The initial thickness of the decellularized samples was 238.5±38.9 µm. In addition, the mechanical properties of fibrin gels was tested, another tissue engineering scaffold used in engineering vascular and cardiac tissue. Fibrin gels were cast into cross-shaped molds with a final concentration of 6.6 mg of fibrin/ml. The average thickness of the fibrin gels was 165.2±67.3 µm. All samples were attached to a biaxial mechanical testing machine (Instron Corporation, Norwood, Mass.) via clamps, submerged in PBS, and stretched equibi-axially to 40% strain. In order to probe the static passive mechanical properties accurately, the samples were stretched in increments of 4% strain and allowed to relax at each strain value for at least 60 seconds. Forces were converted to engineering stress by normalizing the force values with the cross sectional area in the specific axis direction (5 mm×initial thickness). Engineering stress was calculated as the displacement normalized by the initial length. In order to compare the data between the two axes as well as between sample groups, a tangential modulus was calculated as follows:

$$[T(\in=40\% \text{ strain})-T(\in=36\% \text{ strain})]/4\% \text{ strain}$$

where T is engineering stress and $\in$ is engineering strain. The values for the tangential modulus were averaged and compared between the two axes (circumferential and longitudinal) as well as between groups.

Example 6—Assessment of Biocompatibility of Decellularized Organ

To assess biocompatibility, 100,000 mouse embryonic stem cells (mESC) suspended in 1 cc of standard expansion media (Iscove's Modified Dulbecco's Medium (Gibco, Carlsbad, Calif.), 10% Fetal Bovine Serum (HyClone, Logan, Utah), 100 U/ml penicillin-G (Gibco, Carlsbad, Calif.), 100 U/ml streptomycin (Gibco, Carlsbad, Calif.), 2 mmol/L L-glutamine (Invitrogen, Carlsbad, Calif.), 0.1 mmol/L 2-mercaptoethanol (Gibco, Carlsbad, Calif.) were seeded onto the ECM sections and on control plates without specific growth factor stimulation or feeder cell support. 4',6-Diamidino-2-phenylindole (DAPI) was added to the cell culture media at a concentration of 10 µg/ml to label cell nuclei and to allow quantification of cell attachment and expansion. Images were recorded under UV-light and phase contrast at baseline, 24, 48 and 72 hours thereafter using ImagePro Plus 4.5.1 (Mediacybernetics, Silver Spring, Md.) on a Nikon Eclipse TE200 inverted microscope (Fryer Co. Inc., Huntley, Ill.).

The decellularized ECM was compatible with cell viability, attachment and proliferation. Seeded mESCs engrafted on the ECM scaffolds and began to invade the matrix within 72 h of cell seeding.

Example 7—Evaluation of Decellularized Organs

Aortic valve competence and integrity of the coronary vascular bed of SDS decellularized rat heart was assessed by Langendorff perfusion with 2% Evans blue dye. No left ventricular filling with dye was observed, indicating an intact aortic valve. Macroscopically, filling of the coronary arteries up to the fourth branching point was confirmed without signs of dye leakage. In tissue sections, perfusion of large (150 μm) and small (20 μm) arteries and veins was subsequently confirmed by red fluorescence of Evans blue-stained vascular basal membrane.

To confirm the retention of major cardiac ECM components, immunofluorescent staining of SDS decellularized ECM scaffolds was performed. This confirmed the presence of major cardiac ECM components such as collagens I and III, fibronectin and laminin, but showed no evidence of retained intact nuclei or contractile elements including cardiac myosin heavy chain or sarcomeric alpha actin.

Scanning electron micrographs (SEM) of SDS decellularized cardiac ECM demonstrated that fiber orientation and composition were preserved in aortic wall and aortic valve leaflet with an absence of cells throughout the entire tissue thickness. Decellularized left and right ventricular wall retained ECM fiber composition (weaves, struts, coils) and orientation, while myofibers were completely removed. Within the retained ECM of both ventricles, intact vascular basal membranes of different diameters without endothelial or smooth muscle cells were observed. Furthermore, a thin layer of dense epicardial fibers underneath an intact epicardial basal lamina was retained.

To assess mechanical properties of decellularized heart tissue, bi-axial testing was performed and compared to fibrin gels, which is frequently used as an artificial ECM scaffold in cardiac tissue engineering. The normal rat ventricle and decellularized samples were highly anisotropic with respect to the stress-strain behavior. Conversely, in the fibrin gel sample, the stress-strain properties were extremely similar between the two principal directions. The directional dependence of stress-strain behavior was present in all samples in the normal rat ventricle and decellularized groups, and the isotropic nature of the stress-strain properties was typical of all samples in the fibrin gel group.

In order to compare the stress-strain properties between these two groups and also between the principal axes of the hearts, a tangential modulus was calculated at 40% strain (see Example 5 for the equation) in both the circumferential and longitudinal direction. Note that in both directions, the decellularized sample group had a significantly higher modulus than the normal rat ventricle and fibrin gel sample groups. There was a significant difference, however, between the moduli in the two directions for both the normal rat ventricle and the decellularized matrix, but not for the fibrin gel.

For the intact left ventricular tissue, the stress at 40% strain varied between 5 and 14 kPa in the longitudinal direction and between 15 and 24 kPa in the circumferential direction, which is in agreement with previously published data. In both the rat ventricular tissue and the decellularized rat ventricular tissue, the circumferential direction was stiffer than the longitudinal direction, most likely due to muscle fiber orientation of the heart. While the fiber orientation changes through the thickness of the cardiac tissue, the majority of the fibers were oriented in the circumferential direction and thus, this direction would be expected to be stiffer. The decellularized tissue was significantly stiffer than the intact tissue. This also would be expected since the extracellular matrix is stiffer than the cells themselves, and the combination of ECM and cells would likely not be as stiff as just the ECM alone. While the values of the tangential modulus of the decellularized tissue seem rather large, they are only slightly greater than values of the Young's modulus for purified elastin (approximately 600 kPa) and less than Young's modulus of a single collagen fiber (5 Mpa), placing the values determined herein within a reasonable range.

Example 8—Decellularization of Other Organs or Tissues

In addition to rat heart, lung, kidney and liver, similar results were generated by applying the perfusion decellularization protocol described herein to skeletal muscle, pancreas, small and large bowel, esophagus, stomach, spleen, brain, spinal cord and bone.

Example 9—Decellularization of Pig Kidney

Pig kidneys were isolated from heparinized male animals. To allow perfusion of the isolated organs, the renal artery was emulated and blood was washed out with PBS perfusion over 15 minutes. Perfusion with 27 L of 1% SDS in deionized water was performed for 35.5 hours at a pressure of 50-100 mmHg. Perfusion with 1% Triton-X in deionized water was initiated to remove SDS from the ECM scaffold. Washing and buffering of the decellularized kidneys was then performed by perfusion with antibiotic containing PBS for 120 hours to remove detergents and obtain a biocompatible pH.

Organ clearing was observed within two hours of initiating perfusion. Clear white color predominated 12 hours into perfusion. Decellularization was terminated with the organ was white semi-transparent.

Example 10—Transplantation of Decellularized Heart

Hearts from F344 rats were prepared by cannulating the aorta distal to the Ao valve and ligating all other great vessels and pulmonary vessels except the left branch of the pulmonary trunk (distal to its bifurcation) and the inferior vena cava (WC). Decellularization was achieved using Langendorf retrograde coronary perfusion and 2 liters of 1% SDS over 12-16 hours. The hearts were then renatured with 35 mL of 1% Triton-X over 30-40 minutes, and then washed with antibiotic and antifungal-containing PBS for 72 hours. The IVC was ligated before the transplantation.

A large (380 to 400 gram) RNU rat was prepared for reception of the decellularized heart. A blunt-angled mosquito clamp was applied to both the WC and the abdominal Ao of the host animal to ensure isolation of areas of anastomosis. The aorta of the decellularized heart was anastomosed to the host abdominal aorta proximal and inferior to the renal branches using 8-0 silk suture. The left branch of the decellularized heart's pulmonary trunk was anastomosed to the closest region of the host IVC to minimize physical stress on pulmonary trunk.

After both vessels were sewn into the host animal, the clamp was released and the decellularized heart filled with the host animal's blood. The recipient animal's abdominal aortic pressure was observed visually in the decellularized heart and aorta. The decellularized heart became distended and red with blood. Bleeding was minimal at the site of anastomosis. Heparin was administered 3 minutes after clamp release (initiation of perfusion), and the heart was photographed and positioned in the abdomen to minimize stress on the sites of anastomosis. The abdomen was closed in sterile fashion and the animal monitored for recovery. At 55 hours post-transplant, the animal was euthanized and the decellularized heart was explanted for observation. The animals that did not receive heparin showed a large thrombosis in the LV upon dissection and evaluation. Blood was also observed in coronary arteries in both the right and left sides of the heart.

In other transplant experiments, the clamp was released after both vessels were sewn into the host animal, and the decellularized heart filled with the host animal's blood. The recipient animal's abdominal aortic pressure was observed visually in the decellularized heart and aorta. The decellularized heart became distended and red, and bleeding was minimal at the site of anastomosis. Heparin was administered (3000 IU) by IP injection 3 minutes after clamp release (initiation of perfusion). The heart was photographed and positioned in the abdomen to minimize stress on the sites of anastomosis. The abdomen was closed in sterile fashion and the animal monitored for recovery. The animal was found dead from hemorrhage at approximately 48 hours after transplantation. Transplantation time is currently in the 55 to 70 minute range.

Section C. Recellularization

Example 1—Recellularization of Cardiac ECM Slices

To evaluate biocompatibility of decellularised ECM, 1 mm thick slices of one decellularised heart were cultured with myogenic and endothelial cell lines. $2 \times 10^5$ rat skeletal myoblasts, C2C12 mouse myoblasts, human umbilical cord endothelial cells (HUVECs), and bovine pulmonary endothelial cells (BPEC) were seeded onto tissue sections and co-cultured under standard conditions for 7 days. Myogenic cells migrated through and expanded within the ECM and aligned with the original fiber orientation. These myogenic cells showed increased proliferation and fully re-populated large portions of the ECM slice. Endothelial cell lines showed a less invasive growth pattern, forming a monolayer on the graft surface. There were no detectable antiproliferative effects under these conditions.

Example 2—Recellularisation of Cardiac ECM by Coronary Perfusion

To determine the efficiency of seeding regenerative cells onto and into decellularised cardiac ECM by coronary perfusion, a decellularized heart was transferred to an organ chamber and continuously perfused with oxygenised cell culture media under cell culture conditions (5% $CO_2$, 60% humiditiy, 37° C.). $120 \times 10^6$ PKH labelled HUVECs (suspended in 50 ml of endothelial cell growth media) were infused at 40 cm $H_2O$ coronary perfusion pressure. Coronary effluent was saved and cells were counted. The effluent was then recirculated and perfused again to deliver a maximum number of cells. Recirculation was repeated two times. After the third passage, approximately $90 \times 10^6$ cells were retained within the heart. The heart was continuously perfused with 500 ml of recirculating oxygenised endothelial cell culture media for 120 hours. The heart was then removed and embedded for cryosectioning. HUVECs were confined to arterial and venous residues throughout the heart, but were not yet completely dispersed throughout the extravascular ECM.

Example 3—Recellularization of a Decellularized Rat Heart with Neonatal Rat Heart Cells Isolation and preparation of rat neonatal cardiocytes. On day one, eight to ten SPF Fisher-344 neonatal pups, aged 1-3 days (Harlan Labs, Indianapolis, Ind.), were sedated with 5% inhaled Isoflurane (Abbott Laboratories, North Chicago, Ill.), sprayed with 70% EtOH, and a rapid sternotomy was performed in sterile fashion. Hearts were excised and placed immediately into 50 ml conical tube on ice containing HBSS; Reagent #1 from a neonatal cardiomyocyte isolation system (Worthington Biochemical Corporation, Lakewood, N.J.).

Supernatant was removed and whole hearts were washed once with cold HBSS by vigorous swirling. Hearts were transferred to a 100 mm culture dish containing 5 ml cold HBSS, the connective tissue was removed, and remaining tissue was minced into pieces <1 $mm^2$. Additional HBSS was added to bring total plate volume to 9 ml, to which 1 ml Trypsin (Reagent #2, Worthington kit) was added to give a final concentration of 50 µg/ml. Plates were incubated overnight in a 5° C. cooler.

On day two, the plates were removed from the cooler and placed in a sterile hood on ice. Tissue and trypsin-containing buffer were transferred to 50 ml conical tubes on ice using wide-mouth pipettes. Trypsin Inhibitor (Reagent #3) was reconstituted with 1 ml HBSS (Reagent #1) and added to the 50 ml conical tube and gently mixed. The tissue was oxygenated for 60-90 seconds by passing air over the surface of the liquid. The tissue was then warmed to 37° C. and collagenase (300 units/ml) reconstituted with 5 ml Leibovitz L-15 was added slowly. The tissue was placed in a warn (37° C.) shaker bath for 45 minutes. Next, the tissue was titrated ten times using a 10 ml pipet to release the cells (3 mis per second) and then strained through a 0.22 µm filter. The tissue was washed with an 5 additional mis of L-15 media, titrated a second time, and collected in the same 50 ml conical tube. The solution of cells was then incubated at room temperature for 20 minutes, and spun at 50×g for five minutes to pellet the cells. The supernatant was gently removed and the cells were resuspended in the desired volume using Neonatal-Cardiomyocyte Media.

Media and Solutions. All media were sterile filtered and stored in the dark in 5° C. coolers. Worthington Isolation Kit contains a suggested media, Leibovitz L-15, for culture. This media was used for Day Two of the tissue processing only. For plating, an alternate calcium-containing media was used, which is described herein. *Worthington Leibovitz L-15 Media*: Leibovitz media powder was reconstituted using 1 L cell-culture grade water. Leibovitz L-15 media contains 140 mg/ml CaCl, 93.68 mg/ml MgCl, and 97.67 mg/ml MgS. Neonatal-Cardiomyocyte Media: Iscove's Modified Dulbecco's Medium (Gibco, Cat. No. 12440-053) was supplemented with 10% Fetal Bovine Serum (HyClone), 100 U/ml penicillin-G (Gibco), 100 U/ml streptomycin (Gibco), 2 mmol/L L-glutamine (Invitrogen), and 0.1 mmol/L 2-mercaptoethanol (Gibco, Cat. No. 21985-023) and sterile filtered before use. Amphotericine-B was added as needed (0.25 µg/ml final concentration). This media was enhanced with 1.2 mM CaCl (Fisher Scientific, Cat. No. C614-500) and 0.8 mM MgCl (Sigma, Cat. No. M-0250).

In Vitro Culture Analysis of Recellularization. As a step towards creating a bioartificial heart, the isolated ECM was recellularized with neonatal heart-derived cells. Completely decellularized hearts (made as described herein) were injected with a combination of $50\times10^6$ freshly isolated rat neonatal cardiomyocytes, fibrocytes, endothelial and smooth muscle cells. The heart tissue was then sliced and the slices were cultured in vitro to test the biocompatibility of the decellularized ECM and the ability of the resulting constructs to develop into myocardium rings.

Minimal contractions within the resulting rings were observed microscopically after 24 hours, demonstrating that the transplanted cells were able to attach and engraft on the decellularized ECM. Microscopically, cells oriented along the ECM fiber direction. Immunofluorescence staining confirmed the survival and engraftment of cardiomyocytes expressing cardiac myosin heavy chain. Within four days, clusters of contracting cell patches were observed on the decellularized matrix, which progressed to synchronously contracting tissue rings by day 8.

At day 10, these rings were mounted between two rods to measure contractile force under different preload conditions. The rings could be electrically paced up to a frequency of 4 Hz and created contractile force of up to 3 mN under a preload of up to 0.65 g. Thus, with this in vitro tissue culture approach of recellularization, contractile tissue was obtained that generated an equally effective force as that generated by optimized engineered heart tissue rings using artificial ECM constructs.

Recellularization of a Decellularized Heart via Perfusion. Recellularized ($50\times10^6$ freshly isolated rat neonatal cardiomyocytes, fibrocytes, endothelial and smooth muscle cells) scaffolds were mounted in a perfusable bioreactor (n=10) that simulated rat cardiac physiology including pulsatile left ventricular distension with gradually increasing preload and afterload (day 1: preload 4-12 mmHg, afterload 3-7 mmHg), pulsatile coronary flow (day 1: 7 ml/min), and electric stimulation (day 2: 1 Hz) under sterile cardiac tissue culture conditions (5% $CO_2$, 60% $H_2O$, 37° C.). Perfused organ culture was maintained for one to four weeks. Pressures, flows and EKG were recorded for 30 seconds every 15 minutes throughout the entire culture period. Videos of the nascent bioartificial hearts were recorded at days four, six and ten after cell seeding.

At day 10 after cell seeding, a more in-depth functional assessment was performed including insertion of a pressure probe into the left ventricle to record left ventricular pressure (LVP) and video recording of wall motion as the stimulation frequency was gradually increased from 0.1 Hz to 10 Hz and performed pharmacological stimulation with phenylephrine (PE). The recellularized heart showed contractile response to single paces with spontaneous contractions following the paced contractions with corresponding increases in LVP. After a single pace, the heart showed three spontaneous contractions and then converted to a fibrillatory state. Similar to the stimulated contractions, spontaneous depolarizations caused a corresponding increase in LVP and a recordable QRS complex possibly indicating the formation of a developing stable conduction pattern.

Once stimulation frequency was increased to 0.4 Hz, an average of two spontaneous contractions occurred after each induced contraction; at a pacing frequency up to 1 Hz, only one spontaneous contraction occurred; and at a pacing frequency of 5 Hz, no spontaneous contractions occurred. Maximum capture rate was 5 Hz, which is consistent with a refractory period of 250 ms for mature myocardium. After perfusion with 100 µM of PE, regular spontaneous depolarizations occurred at a frequency of 1.7 Hz and were coupled with corresponding increases in LVP.

Histological analysis at day 10 revealed cell dispersion and engraftment throughout the entire thickness of the left ventricular wall (0.5-1.2 mm) Cardiomyocytes aligned with the ventricular fiber direction and formed areas of dense, organized grafts resembling mature myocardium and less dense immature grafts similar to developing myocardium. Immunofluorescence staining for cardiac myosin heavy chain confirmed the cardiomyocyte phenotype. A high capillary density was maintained throughout the newly developed myocardium with an average distance between capillaries of approximately 20 µm, which is similar to that reported for mature rat myocardium. Endothelial cell phenotype was confirmed by immunofluorescent staining for vonWillebrand Factor (vWF). Cell viability was maintained throughout the entire graft thickness, indicating sufficient oxygen and nutrient supply through coronary perfusion.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A perfusion decellularized extracellular matrix portion of a pig, bovine, sheep, or canine organ comprising a non-vasculature decellularized extracellular matrix and vasculature decellularized extracellular matrix, wherein said vasculature decellularized extracellular matrix retains a majority of fluid introduced to said vasculature decellularized extracellular matrix, wherein said vascular decellularized extracellular matrix comprises human cells, wherein said organ is a kidney, lung, liver, pancreas, or spleen, and wherein prior to decellularization the perfusion decellularized extracellular matrix portion included about 10,000,000 cells/mg tissue or wherein the perfusion decellularized extracellular matrix portion is capable of being reseeded with at least 10,000,000 cells.

2. A perfusion decellularized solid organ of a pig, bovine, sheep, or canine comprising a non-vasculature decellularized extracellular matrix and vasculature decellularized extracellular matrix, wherein said vasculature decellularized extracellular matrix retains a majority of fluid introduced to said vasculature decellularized extracellular matrix, wherein said vascular decellularized extracellular matrix comprises human cells, wherein said perfusion decellularized solid organ is a kidney, lung, liver, pancreas, or spleen, and wherein prior to decellularization a perfusion decellularized portion included about 10,000,000 cells/mg tissue or wherein the perfusion decellularized solid organ is capable of being reseeded with at least 10,000,000 cells.

3. The perfusion decellularized extracellular matrix portion of claim 1, wherein said human cells are regenerative cells.

4. The perfusion decellularized extracellular matrix portion of claim 1, wherein said human cells are autologous to a patient.

5. The perfusion decellularized extracellular matrix portion of claim 1, wherein said human cells are allogenic to a patient.

6. The perfusion decellularized extracellular matrix portion of claim 1, wherein said human cells are progenitor cells.

7. The perfusion decellularized extracellular matrix portion of claim 1, wherein said human cells are stem cells.

8. The perfusion decellularized solid organ of claim 2, wherein said human cells are regenerative cells.

9. The perfusion decellularized solid organ of claim 2, wherein said human cells are autologous to a patient.

10. The perfusion decellularized solid organ of claim 2, wherein said human cells are allogenic to a patient.

11. The perfusion decellularized solid organ of claim 2, wherein said human cells are progenitor cells.

12. The perfusion decellularized solid organ of claim 2, wherein said human cells are stem cells.

13. A perfusion decellularized solid organ or portion thereof of a pig, bovine, sheep, or canine comprising a cannula, non-vasculature decellularized extracellular matrix, and vasculature decellularized extracellular matrix, wherein said vasculature decellularized extracellular matrix retains a majority of fluid introduced to said vasculature decellularized extracellular matrix, wherein said vascular decellularized extracellular matrix comprises cells, wherein said perfusion decellularized solid organ or portion thereof is a kidney, lung, liver, pancreas, or spleen, and wherein prior to decellularization a perfusion decellularized portion included about 10,000,000 cells/mg tissue or wherein the perfusion decellularized solid organ or portion thereof is capable of being reseeded with at least 10,000,000 cells.

14. The perfusion decellularized solid organ or portion thereof of claim 13, wherein said cells are regenerative cells.

15. The perfusion decellularized solid organ or portion thereof of claim 13, wherein said cells are autologous to a patient.

16. The perfusion decellularized solid organ or portion thereof of claim 13, wherein said cells are allogenic to a patient.

17. The perfusion decellularized solid organ or portion thereof of claim 13, wherein said cells are progenitor cells.

18. The perfusion decellularized solid organ or portion thereof of claim 13, wherein said cells are stem cells.

19. The perfusion decellularized extracellular matrix portion of claim 1, wherein the pre-perfusion decellularized extracellular matrix portion prior to decellularization included about 10,000,000 cells/mg tissue.

20. The perfusion decellularized extracellular matrix portion of claim 1, wherein the decellularized extracellular matrix portion is capable of being reseeded with at least 10,000,000 cells.

21. The perfusion decellularized solid organ of claim 2, wherein the portion of the pre-perfusion decellularized solid organ prior to decellularization included about 10,000,000 cells/mg tissue.

22. The perfusion decellularized solid organ of claim 2, wherein the perfusion decellularized solid organ is capable of being reseeded with at least 10,000,000 cells.

23. The perfusion decellularized solid organ or portion thereof of claim 13, wherein the portion of a pre-perfusion decellularized solid organ included about 10,000,000 cells/mg tissue.

24. The perfusion decellularized solid organ or portion thereof of claim 13, wherein the perfusion decellularized solid organ or portion is capable of being reseeded with at least 10,000,000 cells.

25. The perfusion decellularized solid organ or portion thereof of claim 13, wherein the perfusion decellularized solid organ or portion is a solid organ.

26. The perfusion decellularized solid organ or portion thereof of claim 13, wherein the perfusion decellularized solid organ or portion is a portion of the solid organ.

* * * * *